United States Patent [19]

Brand et al.

[11] Patent Number: 5,041,618
[45] Date of Patent: Aug. 20, 1991

[54] ALPHA-ARYLACRYLATES AND FUNGICIDES CONTAINING THESE COMPOUNDS

[75] Inventors: Siegbert Brand, Weinheim; Bernd Wenderoth, Lampertheim; Franz Schuetz, Ludwigshafen; Hubert Sauter, Mannheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 367,630

[22] Filed: Jun. 19, 1989

[51] Int. Cl.$^5$ .............................................. C07C 69/76
[52] U.S. Cl. ...................................... 560/104; 560/55
[58] Field of Search .................. 560/104, 55; 514/532, 514/568

[56] References Cited

U.S. PATENT DOCUMENTS 3,468,885 10/1969 Sanne et al. .

OTHER PUBLICATIONS

C A 85(21) 159105g 1976.
C A 82(13) 858291 1975.
Journal of The American Chemical Society, vol. 98, No. 12, Jun. 1976, pp. 3555-3564.
C. A. S. Registry Handbook, 1979, Supplement, pp. 1557 . RH1557, RN-70932-72-8.

*Primary Examiner*—Paul J. Killos
*Attorney, Agent, or Firm*—Oblon, Spivak, McClelland, Maier & Neustadt

[57] ABSTRACT

α-Arylacrylates of the general formula I

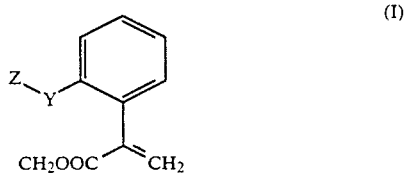

(I)

where
Y is substituted or unsubstituted, alkenylene, alkynylene, O,S(O)$_m$, N, oxycarbonyl, carbonyloxy, oxycarbonylalkylene, carbonyloxyalkylene, oxyalkyleneoxy, oxyalkylene, alkyleneoxy, thioalkylene, azo, carbonylamino, aminocarbonyl or aminocarbonyloxy, and Z is hydrogen, halogen, alkyl, alkenyl, cycloalkyl, alkynyl, aryl, arylalkyl, arylalkenyl, aryloxy, aryloxyalkyl, alkoxyalkyl, haloalkyl, aryloxyalkoxy, alkoxycarbonyl, which are substituted or unsubstituted, or is a 5-membered heterocyclic structure in which two adjacent substituents may form an aromatic or heteroaromatic ring, and fungicides containing these compounds.

3 Claims, No Drawings

ALPHA-ARYLACRYLATES AND FUNGICIDES CONTAINING THESE COMPOUNDS

The present invention relates to novel α-arylacrylates, their preparation and their use as fungicides.

Methyl α-phenylacrylate is known (C.A. Reg. No. 1865-29-8).

We have found that novel α-arylacrylate derivatives of the formula I

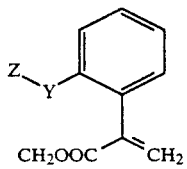

where
Y is unsubstituted or substituted $C_1$–$C_4$-alkylene, unsubstituted or substituted $C_2$–$C_4$-alkenylene, $C_2$–$C_4$-alkynylene, $O, S(O)_m$ (m=0, 1 or 2), unsubstituted or $C_1$–$C_4$-alkyl-substituted N, oxycarbonyl, carbonyloxy, $C_1$–$C_{10}$-oxycarbonylalkylene, $C_1$–$C_{10}$-carbonyloxyalkylene, $C_2$–$C_{10}$-oxyalkylene, $C_1$–$C_{10}$-oxyalkyleneoxy, $C_1$–$C_{10}$-alkyleneoxy, $C_1$–$C_{10}$-thioalkylene, azo, unsubstituted or $C_1$–$C_4$-alkyl-substituted carbonylamino, unsubstituted or $C_1$–$C_4$-alkyl-substituted aminocarbonyl or unsubstituted or $C_1$–$C_4$-alkyl-substituted aminocarbonyloxy and Z is hydrogen, halogen, $C_1$–$C_{18}$-alkyl, $C_2$–$C_{18}$-alkenyl, $C_3$–$C_8$-cycloalkyl, $C_2$–$C_4$-alkynyl, aryl, aryl-$C_1$–$C_{10}$-alkyl, aryl-$C_2$–$C_{10}$-alkenyl, aryloxy, aryloxy-$C_1$–$C_{10}$-alkyl, alkoxy-$C_1$–$C_{10}$-alkyl, halo-$C_1$–$C_{10}$-alkyl, aryloxy-$C_1$–$C_4$-alkoxy, $C_1$–$C_4$-alkoxycarbonyl, which are unsubstituted or substituted by halogen, cyano, nitro, $C_1$–$C_4$-alkyl, $C_2$–$C_4$-alkenyl, $C_1$–$C_4$-alkoxy, $C_1$–$C_4$-haloalkyl, $C_2$–$C_4$-haloalkenyl, $C_1$–$C_4$-alkoxycarbonyl, unsubstituted or substituted phenyl or unsubstituted or substituted phenoxy, or is C-bonded, unsubstituted or substituted 5-membered heterocyclic structure which contains one to four indentical or different heteroatoms, i.e. nitrogen, oxygen or sulfur in that two adjacent substituents may form an aromatic or heteroaromatic ring which may be bonded to an ethylene unit, have a very good fungicidal action which is better than that of the known fungicides.

Y is preferably methylene, ethylene, ethenylene, ethynylene, O, S, methyleneoxy, ethyleneoxy, oxymethylene, thiomethylene, carbonyloxy, oxycarbonyl, carbonyloxymethylene or —HN—CO—O—.

Z is preferably hydrogen, halogen (e.g. fluorine, chlorine or bromine), $C_1$–$C_{18}$-alkyl, (e.g. methyl, ethyl, n-or isopropyl, n-, sec-, iso- or tert-butyl, 3-methylbutyl, 2,2-dimethylpropyl, 1,1-dimethylpropyl, 3-hexyl, n-pentyl, n-hexyl, n-heptyl, n-octyl, n-nonyl, n-decyl, n-pentadecyl, n-heptadecyl or 2,6-dimethylhept-1-yl), cyanomethyl, $C_2$–$C_9$-alkenyl (e.g. vinyl, prop-2-en-2-yl, prop-1-en-1-yl, but-2-en-2-yl, 2-methylprop-1-en-1-yl, allyl, but-2-en-1-yl, 3-methylbut-2-en-1yl, penta-1,3-dien-1-yl, 2,6-dimethylhepta-1,5-dien-1-yl or 2,6-dimethylhept-5-en-1-yl); $C_2$-alkynyl (e.g. ethynyl or 2-phenylethynyl), $C_1$- or $C_2$-alkoxy-$C_1$- or -$C_2$-alkyl (methoxymethyl, ethoxymethyl or 1-methoxyethyl), $C_3$–$C_6$-cycloalkyl (e.g. cyclopropyl, cyclobutyl, cyclopentyl, cyclohexyl or 1-methylcyclopropyl), and the following substituted cyclopropyl radicals being examples:

2,2-dichloro-1-methylcyclopropyl (A1)
2,2-dichloro-3,3-dimethylcyclopropyl (A2)
2,2,3,3-tetramethylcyclopropyl (A3)
2-(2'-methyl-1'-propenyl)-3,3-dimethylcyclopropyl (A4)
2-(2',2'-difluorovinyl)-3,3-dimethylcyclopropyl (A5)
2-(2',2'-dichlorovinyl)-3,3-dimethylcyclopropyl (A6)
2-(2',2'-dibromovinyl)-3,3-dimethylcyclopropyl (A7)
2-phenylcyclopropyl (A8)
2-(4'-chlorophenyl)-cyclopropyl (A9)
2,2-dichloro-3-phenylcyclopropyl (A10)
2-carbomethoxycyclopropyl (A11)

or halo-$C_1$- or $C_2$-alkyl (e.g. chloromethyl, 1-chloroethyl, dichloromethyl, trichloromethyl, bromomethyl or trifluoromethyl), phenyl, substituted phenyl, such as halophenyl (e.g. 2-fluoro, 3-fluoro-, 4-fluoro-, 6-fluoro-, 2-chloro-, 2,4-difluoro-, 2,6-difluoro, 2,3,4,5,6-pentafluoro-, 3-chloro-, 4-chloro-, 2,4-dichloro-, 2,5-dichloro-, 2,6-dichloro-, 3,4-dichloro-, 3,5-dichloro-, 2,4,5-trichloro-, 2,3,4,5,6-pentachloro-, 2-bromo-, 3-bromo-, or 4-bromophenyl);

$C_1$–$C_4$-alkylphenyl (e.g. 2-methyl-, 3-methyl-, 4-methyl-, 2,3-dimethyl-, 2,4-dimethyl-, 2,5-dimethyl-, 2,6-dimethyl-, 3,4-dimethyl-, 3,5-dimethyl-, 2,4,6-trimethyl-or 4-tert-butylphenyl); arylphenyl (e.g. 2-phenyl- or 4-phenylphenyl); halo-$C_1$-alkylphenyl (e.g. 2-trifluoro-, 3-trifluoro-or 4-trifluoromethylphenyl); $C_1$–$C_4$-alkoxyphenyl (e.g. 2-methoxy-, 3-methoxy-, 4-methoxy-, 3,4-dimethoxy-, 3,4,5-trimethoxy- or 4-tert-butoxyphenyl); 2-, 3- or 4-phenoxyphenyl;

Substituted benzyl (e.g. halobenzyl, such as 2-fluoro-, 3-fluoro-, 4-fluoro-, 2-chloro-, 3-chloro-, 4-chloro-, 2-chloro-, 6-fluoro-, 2,4-dichloro-, 2,6-dichloro-, 3,5-dichloro-, 2,4,6-trichloro-, 2-bromo-, 3-bromo-, 4-bromo-, 2-methyl-, 3-methyl-, 4-methyl-, 4-tert-butyl-, 2,4-dimethyl-, 2,6-dimethyl-, 2,4,6-trimethyl-, 2-methoxy-, 3-methoxy-, 4-methoxy-, 2-trifluoromethyl-, 3-trifluoromethyl-, 4-trifluoromethyl-, 4-tert-butoxy-, 4-phenoxy-or 4-phenylbenzyl, α-methyl-α-ethyl-, α-isopropyl-, α-hydroxy-, 2-methoxy-α-hydroxy-, 4-methoxy-α-hydroxy-, 3,4-dimethoxy-α-hydroxy-, 2-methoxy-α-methoxy-, 4-methoxy-α-methoxy- or 3,4-dimethoxy-α-methoxybenzyl); unsubstituted or substituted phenethyl (e.g. phenyl-, 1-methyl-2-phenyl-, 2-(para-tert-butylphenyl)-, 2-(para-tert-butylphenyl)-1-methyl-, 2-(ortho-chlorophenyl)-, 2-(meta-chlorophenyl)- or 2-(para-chlorophenyl)ethyl); unsubstituted or substituted or styryl (e.g. styryl or 2'-chloro-, 3'-chloro-, 4'-chloro-, 2',4'-dichloro-, 2'-fluoro, 4'-fluoro-, 2'-methyl-, 4'-methyl-, 4'-tert-butyl-, 2'-methoxy-, 4'-methoxy- or 4'-phenoxystyryl); phenyl-$C_3$–$C_6$-alkyl (e.g. 3-phenylpropyl, 2-methyl-3-phenylpropyl, 4-phenylbutyl, 5-phenylpentyl, 6-phenylhexyl or 3-(4'-tert-butylphenyl)-2-methylpropyl);

aryloxy, such as substituted phenoxy (e.g. 2-chloro-, 3-chloro-, 4-chloro-, 2-methyl-, 4-methyl-, 2-methoxy-, 4-methoxy-, 2-trifluoromethyl- or 4-trifluoromethylphenoxy); aryloxy-$C_1$–$C_6$-alkyl, such as unsubstituted or substituted phenoxymethyl (e.g. 2-chloro-, 4-chloro-, 2-methyl-, 4-methyl-, 2-methoxy-, 4-methoxy- or 4-tert-butylphenoxymethyl); unsubstituted or substituted phenoxyethyl (e.g. 2-chloro-, 4-chloro-, 4-fluoro-, 2-methyl-, 4-methyl-, 2-methoxy-, 4-methoxy- or 4-tert-butylphenoxyethyl), unsubstituted or substituted $C_3$-$C_6$-phenoxyalkyl (e.g. phenoxypropyl, 3-(ortho-chlorophenoxy)-propyl, 3-(para-chlorophenoxy)-propyl, 4-phenoxybutyl, 4-(ortho-chlorophenoxy)-butyl, 4-(para-chlorophenoxy)-butyl, 5-phenoxypentyl, 5-(ortho-chlorophenoxy)-pentyl, 5-(para-chlorophenoxy)-pentyl or 6-phenoxyhexyl); phenoxyethoxy; methoxycarbonyl or tert-butoxycarbonyl; unsubstituted or substituted hetaryl (e.g. furyl, 2-furyl, 3-furyl, 5-nitro-2- and -3-furyl, 5-chloro-2- and -3-furyl, benzofuran-2- and -3-yl, thienyl, 2-thienyl, 3-thienyl, 5-nitro-2- and -3-thienyl, 5-chloro-2-and -3-thienyl and benzothien-2- and -3-yl);

N-methylpyrrol-2- and -3-yl, N-methylpyrazol-3-, -4- and -5-yl, N-methylimidazol-2-, -4- and -5-yl, 1-methyl-1,2,3-triazol-4- and -5-yl, 1-methyl-1,2,4-triazol-3- and -5-yl, 1-methyltetrazol-5-yl, isoxazol-3-, -4- and -5-yl, benzisoxazol-3-yl, benzoxazol-2-yl, oxazol-2-, -4- and -5-yl, thiazol-2-, -4- and -5-yl, benzothiazol-2-yl, benzoisothiazol-3-yl, isothiazol-3-, -4- and -5-yl, 1,2,3-thiadiazol-4-yl, 1,2,4-thiadiazol-5-yl, 1,3,4-thiadiazol-3-yl or 1,3-thiazolo[4,5-b]pyridin-2-yl) and substituted hetarylalkenyl (e.g. 2-(2'- and 3'-furyl)-, 2-(5'-nitro-2'- and -3'-furyl)-, 2-(2'- and 3'-thienyl)-and 2-(5'-nitro-2'- and -3'-thienyl)-ethenyl).

The compounds of the formula I can be prepared, for example, by the reactions shown in Scheme 1.

The α-ketocarboxylates of the formula IV can be converted into the acrylates of the formula I by a Wittig reaction with methylenetriphenylphosphorane in a conventional manner in the presence of a base, e.g. n-butyllithium, potassium tert-butylate, sodium hydride or sodium methylate (cf. G. Wittig and U. Schöllkopf, Org. Synth., Coll. Vol. V (1973), 751).

Preparation of the α-ketoesters of the formula IV is known (EP 178826).

For example, the aromatic Grignard compounds VII are reacted with imidazolidenes of the formula VIII (J. S. Nimitz and H. S. Mosher, J. Org. Chem. 46 (1981), 211), where Y and Z have the abovementioned meanings.

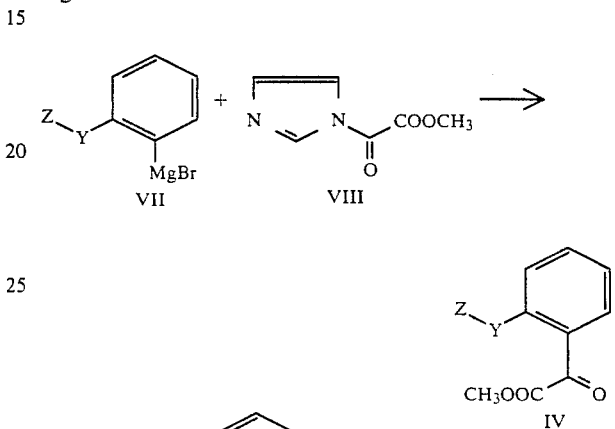

Scheme 1

R = $CH_3$ or $C_2H_5$

The phenylacetates of the formula II are converted in a conventional manner via the 3-aryl-2-oxosuccinates III into the methyl α-arylacrylates I (cf. E. Galantay et al., J. Org. Chem. 35 (1970), 4277). For this purpose, the phenylacetate (II) is acylated with a dialkyl oxalate with the aid of a base, e.g. sodium methylate or sodium ethylate, to give the diesters III and the latter are subjected to an addition reaction with formaldehyde. By hydrolysis with an aqueous base, e.g. potassium carbonate, the atropaic acid derivatives I are obtained. The compounds of the formula I can be prepared directly from phenylacetates II with paraformaldehyde, potassium carbonate and a catalytic amount of phase transfer catalyst, e.g. tetrabutylammonium iodide, in, for example, toluene [cf. W. Seitz and A. Michel, DE 3 317 356].

The oxidation of substituted acetophenones (IX) with potassium permanganate in pyridine/water/potassium hydroxide

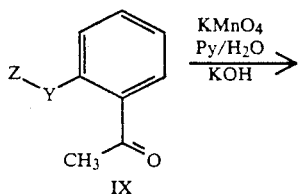

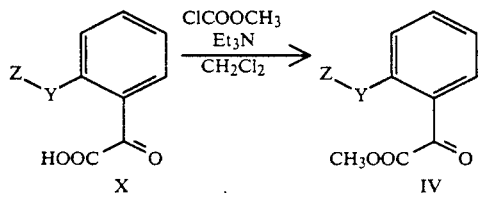

(cf. J. W. F. McOmie and S. D. Thata, J. Chem. Soc. 1965, 5298) gives the phenylketoacids X, which can be esterified with, for example, methyl chloroformate/triethylamine to give the α-ketoesters IV (cf. J. M. Domagala, Tetrahedron Lett. 21 (1980), 4957).

The benzyl cyanides V can be converted into the α-arylacrylonitriles of the formula VI by treating them with a base, e.g. sodium methylate, and formaldehyde (cf. J. M. Stewart and C. H. Chang, J. Org. Chem. 21 (1956), 635).

The nitriles VI are converted into the acrylates of the formula I with a methanolic mineral acid, e.g. hydrochloric acid or sulfuric acid (cf. E. N. Zil'berman, Russ. Chem. Rev. 31 (1962), 615).

The Examples which follow illustrate the preparation of the novel compounds of the formula I.

EXAMPLE 1

Preparation of methyl 2-[2'-cinnamoyloxymethyl)-phenyl]acrylate (No. 866)

a) Preparation of methyl ortho-bromomethylphenylglyoxalate 50.0 g (0.28 mole) of methyl ortho-methylphenylglyoxalate are dissolved in 3 liters of carbon tetrachloride, together with 50.0 g (0.28 mole) of freshly crystallized N-bromosuccinimide. The reaction mixture is exposed to a 300 W Hg vapor lamp for one hour and is evaporated down to 1 liter, the organic phase is washed with 3×200 ml of water and dried over sodium sulfate, the solvent is distilled off and the residue is chromatographed over silica gel with 1:9 methyl tert-butyl ether/hexane. 10 g of the ketoesters (II, YZ=CH$_3$) and 21.1 g of the benzyl bromide (II, Y-Z=CH$_2$Br) (37%, based on converted ketoester) are obtained as a yellow oil.

$^1$H (CDCl$_3$): δ=3.97(s,3H), 4.90(s,2H), 7.4–7.8(m,4H) IR (film): 2955, 1740, 1690, 1435, 1318, 1207, 999 cm$^{-1}$.

b) Preparation of methyl 2-(cinnamoylmethyl)-phenylglyoxalate 10.4 g (56 millimoles) of potassium transcinnamate and 12.0 g (47 millimoles) of methyl orthobromomethylphenylglyoxalate are dissolved in 250 ml of N-methylpyrrolidone, a pinch of potassium iodide is added and the mixture is stirred for 15 hours at room temperature (23° C.). Thereafter, the mixture is poured onto 500 ml of ice water and extracted with 3×200 ml of methyl tert-butyl ether and the organic phase is washed with water, dried over sodium sulfate and evaporated down in a rotary evaporator. The yield of ketoester is 15.0 g (99%). Thin layer chromatographic analysis shows that it is virtually pure.

$^1$H-NMR (CDCl$_3$): δ=3.97 (s, 3H), 5.62 (s, 2H); 6.55 (d, J=10 Hz; 1H); 7.3–7.85 (m, 9H); 7.77 (d, J=10 Hz, 1H) IR (film): 1728, 1688, 1638, 1210, 1168, 998, 978, 765 cm$^{-1}$.

c) Preparation of methyl 2-[2'-(cinnamoyloxymethyl)-phenyl]-acrylate (No. 866)

10.5 g (26 millimoles) of methyltriphenylphosphonium iodide in 100 ml of anhydrous tetrahydrofuran are initially taken under a nitrogen atmosphere. 16.5 ml of a 1.6M solution of n-butyllithium in n-hexane are added dropwise at 0° C. and stirring is continued for 1 hour at 0° C. After the mixture has been cooled to −78° C., 7.5 g (23 millimoles) of the ketoester obtained according to b), in 50 ml of tetrahydrofuran, are slowly added dropwise. The mixture is allowed to reach room temperature and is stirred for a further 12 hours. It is poured into ammonium chloride solution and extracted with methyl tert-butyl ether. The organic phases are washed with water, dried over sodium sulfate and evaporated down. The product is obtained by column chromatography over silica gel using 1:9 methyl tert-butyl ether/n-hexane. 2.1 g (28%) of the abovementioned acrylate are obtained as an oil.

$^1$H-NMR (CDCl$_3$): δ=3.75 (s, 3H); 5.18 (s, 2H); 5.8 (d, J=1 Hz, 1H); 6.42 (d, J=10 Hz, 1H); 6.60 (d, J=1 Hz, 1H); 7.15–7.60 (m, 9H); 7.68 (d, J=10 Hz; 1H).
IR (film): 1719, 1637, 1311, 1204, 1164, 768 cm$^{-1}$.

EXAMPLE 2

Preparation of the Intermediates

Preparation of methyl 2-methylphenylglyoxalate 1.4 g (10 millimoles) of ortho-methylacetophenone, 2.0 g of potassium hydroxide, 200 ml of pyridine and 100 ml of water are initially taken at +10° C. 5 g of potassium permanganate in 250 ml of water are added dropwise and the mixture is stirred for 2 hours at this temperature. Thereafter, sodium bisulfite solution is added dropwise until the red coloration of the mixture vanishes. The mixture is filtered, the filtrate is acidified with concentrated hydrochloric acid and filtered again and this filtrate is extracted with 5×50 ml of methyl tert-butyl ether. The organic phase is dried over sodium sulfate and evaporated down and the residue is then directly reacted further (ratio of ketoacid to benzoic acid 8–9:1 according to $^1$H-NMR). 2.0 g of the above mixture in 20 ml of dichloromethane are initially taken and 1.6 g (16 millimoles) of triethylamine are added. 1.5 g (16 millimoles) of methyl chloroformate are added dropwise at room temperature. After 1 hour at this temperature, the mixture is extracted with phosphate buffer (pH 7) and evaporation and distillation are carried out.

Bp. 95°–99° C./0.4 mbar; yield: 0.92 g (51%).

IR (film): 1740, 1686, 1602, 1457, 1317, 1285, 1203, 1002, 739 cm$^{-1}$.

EXAMPLE 3

Preparation of methyl 2-[2'-(benzyloxyphenyl]-acrylate (No. 446)

25.6 g (0.10 mole) of methyl ortho-benzyloxyphenylacetate, 4.5 g (0.15 mole) of paraformaldehyde, 23.5 g (0.16 mole) of potassium carbonate and 600 mg (2 millimoles) of tetrabutylammonium iodide are added to 50 ml of toluene. The mixture is stirred for 3-4 hours at 80°-85° C., after which it is cooled and 50 ml of water are added. The mixture is shaken, the phases are separated, the aqueous phase is extracted with 2×50 ml of toluene and the toluene and the organic phase are extracted with 2×50 ml of saturated sodium chloride solution. Drying with $Na_2SO_4$ and evaporation give a yellowish oil, which is chromatographed over silica gel using 1:2 methyl tert-butyl ether/hexane. Yield: 16.4 g (61%).

IR (film): 1727, 1602, 1495, 1451, 1276, 1242, 1268, 753, 735, 696 cm$^{-1}$.

$^1$H-NMR (CDCl$_3$): $\delta$=3.60 (s, 3H); 5.07 (s, 2H); 5.23 (d, J=1 Hz; 1H); 6.26 (d, J=1 Hz; 1H); 6.8-7.0 (m, 2H); 7.1-7.4 (m, 7H).

EXAMPLE 4

Preparation of 2'(2'-methoxycarbonylethen-1'-yl)-benzyltriphenylphosphonium bromide (No. 926)

14 g (80 millimoles) of methyl 2-(2'-methylphenyl)-acrylate, 28.5 g (160 millimoles) of N-bromosuccinimide and 500 ml of carbon tetrachloride are combined and the refluxed mixture is exposed for 3 hours to a mercury vapor lamp (300 W). The mixture is cooled, washed with water, dried with sodium sulfate and then evaporated down. The crude product (methyl 2-(2'-bromomethylphenyl)-acrylate (No. 925)) is dissolved in 500 ml of tetrahydrofuran, 21 g (80 millimoles) of triphenylphosphine are added and the mixture is kept for 15 hours at 23° C. and the boiled for 4 hours at 70° C. The mixture is cooled and filtered under suction, and the residue is washed with methyl tert-butyl ether and dried under reduced pressure to give 16.0 g (39%) of a white powder of melting point 145°-147° C.

$^1$H-NMR (CDCl$_3$; No. 925): $\delta$=3.78 (s, 3H); 4.42 (s, 2H); 5.90 (d, J=1 Hz; 1H); 6.65 (d, J=1 Hz, 1H); 7.1-7.5 (m, 4H).

$^1$H-NMR (CDCl$_3$; No. 926): $\delta$=3.62 (s, 3H); 5.07 (sbr, 1H); 5.15 (d, J=1 Hz, 2H); 6.27 (sbr; 1H); 7.0-7.85 (m, 19H).

| No. | Z | Y | Data |
|---|---|---|---|
| 1 | H | —CH=CH— | |
| 2 | CH$_3$ | —CH=CH— | |
| 3 | C$_2$H$_5$ | —CH=CH— | |
| 4 | n-C$_3$H$_7$ | —CH=CH— | |
| 5 | iso-C$_3$H$_7$ | —CH=CH— | |
| 6 | n-C$_4$H$_9$ | —CH=CH— | |
| 7 | (CH$_3$)$_2$CHCH$_2$ | —CH=CH— | |
| 8 | CH$_3$CH$_2$CH(CH$_3$) | —CH=CH— | |
| 9 | tert.C$_4$H$_9$ | —CH=CH— | |
| 10 | CH$_3$CH$_2$C(CH$_3$)$_2$ | —CH=CH— | |
| 11 | (CH$_3$)$_2$CCH$_2$ | —CH=CH— | |
| 12 | (CH$_3$)$_2$CHCH$_2$CH$_2$ | —CH=CH— | |
| 13 | CH$_3$CH$_2$CH$_2$CH(C$_2$H$_5$) | —CH=CH— | |
| 14 | n-C$_5$H$_{11}$ | —CH=CH— | |
| 15 | n-C$_6$H$_{13}$ | —CH=CH— | |
| 16 | n-C$_7$H$_{15}$ | —CH=CH— | |
| 17 | n-C$_8$H$_{17}$ | —CH=CH— | |
| 18 | n-C$_9$H$_{19}$ | —CH=CH— | |
| 19 | n-C$_{10}$H$_{21}$ | —CH=CH— | |
| 20 | n-C$_{15}$H$_{31}$ | —CH=CH— | |
| 21 | n-C$_{17}$H$_{35}$ | —CH=CH— | |
| 22 | CH$_2$=CH | —CH=CH— | |
| 23 | CH$_2$=C(CH$_3$) | —CH=CH— | |
| 24 | CH$_3$CH=CH | —CH=CH— | |
| 25 | CH$_3$CH=C(CH$_3$) | —CH=CH— | |
| 26 | (CH$_3$)$_2$C=CH | —CH=CH— | |
| 27 | CH$_2$=CHCH$_2$ | —CH=CH— | |
| 28 | CH$_3$CH=CHCH$_2$ | —CH=CH— | |
| 29 | (CH$_3$)$_2$C=CHCH$_2$ | —CH=CH— | |
| 30 | CH$_3$CH=CH—CH=CH | —CH=CH— | |
| 31 | (CH$_3$)$_2$C=CHCH$_2$CH$_2$C(CH$_3$)=CH | —CH=CH— | |
| 32 | (CH$_3$)$_2$CHCH$_2$CH$_2$CH$_2$CH(CH$_3$)CH$_2$ | —CH=CH— | |
| 33 | (CH$_3$)$_2$C=CHCH$_2$CH$_2$CH(CH$_3$)CH$_2$ | —CH=CH— | |
| 34 | HC≡C | —CH=CH— | |
| 35 | C$_6$H$_5$—C≡C | —CH=CH— | |
| 36 | CH$_3$OCH$_2$ | —CH=CH— | |
| 37 | C$_2$H$_5$OCH$_2$ | —CH=CH— | |
| 38 | CH$_3$CH(OCH$_3$) | —CH=CH— | |
| 39 | CN—CH$_2$ | —CH=CH— | |
| 40 | cyclopropyl | —CH=CH— | |
| 41 | cyclobutyl | —CH=CH— | |
| 42 | cyclopentyl | —CH=CH— | |
| 43 | cyclohexyl | —CH=CH— | |
| 44 | 1-methylcyclopropyl | —CH=CH— | |
| 45 | 2,2-dichloro-1-methyl-cyclopropyl | —CH=CH— | |
| 46 | 2,2-dichloro-3,3-dimethyl-cyclopropyl | —CH=CH— | |
| 47 | 2,2,3,3-tetramethylcyclopropyl | —CH=CH— | |
| 48 | 2-(2'-methyl-1'-propenyl-)-3,3-dimethylcyclopropyl | —CH=CH— | |
| 49 | 2-(2',2'-difluorovinyl)-3,3-dimethylcyclopropyl | —CH=CH— | |
| 50 | 2-(2',2'-dichlorovinyl)-3,3-dimethylcyclopropyl | —CH=CH— | |
| 51 | 2-(2',2'dibromovinyl)-3,3-dimethylcyclopropyl | —CH=CH— | |

-continued

| | | |
|---|---|---|
| 52 | 2-phenylcyclopropyl | —CH=CH— |
| 53 | 2-(4'-chlorophenyl)cyclopropyl | —CH=CH— |
| 54 | 2,2-dichloro-3-phenylcyclopropyl | —CH=CH— |
| 55 | 2-carbomethoxy-cyclopropyl | —CH=CH— |
| 56 | $ClCH_2$ | —CH=CH— |
| 57 | $Cl_2CH$ | —CH=CH— |
| 58 | $Cl_3C$ | —CH=CH— |
| 59 | $BrCH_2$ | —CH=CH— |
| 60 | $CF_3$ | —CH=CH— |
| 61 | $CH_3CH(Cl)$ | —CH=CH— |
| 62 | $C_6H_5$ (=phenyl) | —CH=CH— |
| 63 | $2\text{-}CH_3\text{—}C_6H_4$ | —CH=CH— |
| 64 | $3\text{-}CH_3\text{—}C_6H_4$ | —CH=CH— |
| 65 | $4\text{-}CH_3\text{—}C_6H_4$ | —CH=CH— |
| 66 | $2,3\text{-}(CH_3)_2\text{—}C_6H_3$ | —CH=CH— |
| 67 | $2,4\text{-}(CH_3)_2\text{—}C_6H_3$ | —CH=CH— |
| 68 | $2,6\text{-}(CH_3)_2\text{—}C_6H_3$ | —CH=CH— |
| 69 | $3,4\text{-}(CH_3)_2\text{—}C_6H_3$ | —CH=CH— |
| 70 | $3,5\text{-}(CH_3)_2\text{—}C_6H_3$ | —CH=CH— |
| 71 | $2,4,6\text{-}(CH_3)_2\text{—}C_6H_2$ | —CH=CH— |
| 72 | $4\text{-}t\text{-}C_4H_9\text{—}C_6H_4$ | —CH=CH— |
| 73 | $2\text{-}C_6H_5\text{—}C_6H_4$ | —CH=CH— |
| 73 | $2\text{-}C_6H_5\text{—}C_6H_4$ | —CH=CH— |
| 74 | $4\text{-}C_6H_5\text{—}C_6H_4$ | —CH=CH— |
| 75 | $2\text{-}Cl\text{—}C_6H_4$ | —CH=CH— |
| 76 | $3\text{-}Cl\text{—}C_6H_4$ | —CH=CH— |
| 77 | $4\text{-}Cl\text{—}C_6H_4$ | —CH=CH— |
| 78 | $2,4\text{-}Cl_2\text{—}C_6H_3$ | —CH=CH— |
| 79 | $2,5\text{-}Cl_2\text{—}C_6H_3$ | —CH=CH— |
| 80 | $2,6\text{-}Cl_2\text{—}C_6H_3$ | —CH=CH— |
| 81 | $3,4\text{-}Cl_2\text{—}C_6H_3$ | —CH=CH— |
| 82 | $3,5\text{-}Cl_2\text{—}C_6H_3$ | —CH=CH— |
| 83 | $2,4,5\text{-}Cl_3\text{—}C_6H_2$ | —CH=CH— |
| 84 | $2,3,4,5,6\text{-}Cl_5\text{—}C_6$ | —CH=CH— |
| 85 | $6\text{-}F,2\text{-}Cl\text{—}C_6H_3$ | —CH=CH— |
| 86 | $2\text{-}F\text{—}C_6H_4$ | —CH=CH— |
| 87 | $3\text{-}F\text{—}C_6H_4$ | —CH=CH— |
| 88 | $4\text{-}F\text{—}C_6H_4$ | —CH=CH— |
| 89 | $2,4\text{-}F_2\text{—}C_6H_3$ | —CH=CH— |
| 90 | $2,6\text{-}F_2\text{—}C_6H_3$ | —CH=CH— |
| 91 | $2,3,4,5,6\text{-}F_5\text{—}C_6$ | —CH=CH— |
| 92 | $2\text{-}Br\text{—}C_6H_4$ | —CH=CH— |
| 93 | $3\text{-}Br\text{—}C_6H_4$ | —CH=CH— |
| 94 | $4\text{-}Br\text{—}C_6H_4$ | —CH=CH— |
| 95 | $2\text{-}CF_3\text{—}C_6H_4$ | —CH=CH— |
| 96 | $3\text{-}CF_3\text{—}C_6H_4$ | —CH=CH— |
| 97 | $4\text{-}CF_3\text{—}C_6H_4$ | —CH=CH— |
| 98 | $2\text{-}OCH_3\text{—}C_6H_4$ | —CH=CH— |
| 99 | $3\text{-}OCH_3\text{—}C_6H_4$ | —CH=CH— |
| 100 | $4\text{-}OCH_3\text{—}C_6H_4$ | —CH=CH— |
| 101 | $3,4\text{-}(OCH_3)_2\text{—}C_6H_3$ | —CH=CH— |
| 102 | $3,4,5\text{-}(OCH_3)_3\text{—}C_6H_2$ | —CH=CH— |
| 103 | $4\text{-}t\text{-}C_4H_9O\text{—}C_6H_4$ | —CH=CH— |
| 104 | $2\text{-phenoxy-}C_6H_4$ | —CH=CH— |
| 105 | $3\text{-phenoxy-}C_6H_4$ | —CH=CH— |
| 106 | $4\text{-phenoxy-}C_6H_4$ | —CH=CH— |
| 107 | $C_6H_5\text{—}CH_2$ | —CH=CH— |
| 108 | $2\text{-}F\text{—}C_6H_4\text{—}CH_2$ | —CH=CH— |
| 109 | $3\text{-}F\text{—}C_6H_4\text{—}CH_2$ | —CH=CH— |
| 110 | $4\text{-}F\text{—}C_6H_4\text{—}CH_2$ | —CH=CH— |
| 111 | $2\text{-}Cl\text{—}C_6H_4\text{—}CH_2$ | —CH=CH— |
| 112 | $3\text{-}Cl\text{—}C_6H_4\text{—}CH_2$ | —CH=CH— |
| 113 | $4\text{-}Cl\text{—}C_6H_4\text{—}CH_2$ | —CH=CH— |
| 114 | $2\text{-}Cl, 6F\text{—}C_6H_3\text{—}CH_2$ | —CH=CH— |
| 115 | $2,4\text{-}Cl_2\text{—}C_6H_3\text{—}CH_2$ | —CH=CH— |
| 116 | $2,6\text{-}Cl_2\text{—}C_6H_3\text{—}CH_2$ | —CH=CH— |
| 117 | $3,5\text{-}Cl_2\text{—}C_6H_3\text{—}CH_2$ | —CH=CH— |
| 118 | $2,4,6\text{-}Cl_3\text{—}C_6H_2\text{—}CH_2$ | —CH=CH— |
| 119 | $2\text{-}CH_3\text{—}C_6H_4\text{—}CH_2$ | —CH=CH— |
| 120 | $3\text{-}CH_3\text{—}C_6H_4\text{—}CH_2$ | —CH=CH— |
| 121 | $4\text{-}CH_3\text{—}C_6H_4\text{—}CH_2$ | —CH=CH— |
| 122 | $4\text{-}t\text{-}C_4H_9\text{—}C_6H_4\text{—}CH_2$ | —CH=CH— |
| 123 | $2,4\text{-}(CH_3)_2\text{—}C_6H_3\text{—}CH_2$ | —CH=CH— |
| 124 | $2,6\text{-}(CH_3)_2\text{—}C_6H_3\text{—}CH_2$ | —CH=CH— |
| 125 | $2,4,6\text{-}(CH_3)_3\text{—}C_6H_2\text{—}CH_2$ | —CH=CH— |
| 126 | $2\text{-}OCH_3\text{—}C_6H_4\text{—}CH_2$ | —CH=CH— |
| 127 | $3\text{-}OCH_3\text{—}C_6H_4\text{—}CH_2$ | —CH=CH— |
| 128 | $4\text{-}OCH_3\text{—}C_6H_4\text{—}CH_2$ | —CH=CH— |
| 129 | $2\text{-}CF_3\text{—}C_6H_4\text{—}CH_2$ | —CH=CH— |
| 130 | $3\text{-}CF_3\text{—}C_6H_4\text{—}CH_2$ | —CH=CH— |
| 131 | $4\text{-}CF_3\text{—}C_6H_4\text{—}CH_2$ | —CH=CH— |
| 132 | $4\text{-}O\text{-}t\text{-}C_4H_9\text{—}C_6H_4\text{—}CH_2$ | —CH=CH— |

-continued

| | | |
|---|---|---|
| 133 | 4-O—C₆H₅—C₆H₄—CH₂ | —CH=CH— |
| 134 | 4-C₆H₅—C₆H₄—CH₂ | —CH=CH— |
| 135 | 2-Br—C₆H₄—CH₂ | —CH=CH— |
| 136 | 3-Br—C₆H₄—CH₂ | —CH=CH— |
| 137 | 4-Br—C₆H₄—CH₂ | —CH=CH— |
| 138 | C₆H₅—CH(CH₃) | —CH=CH— |
| 139 | C₆H₅—CH(C₂H₅) | —CH=CH— |
| 140 | C₆H₅—CH(iso-C₃H₇) | —CH=CH— |
| 141 | C₆H₅—CH(OH) | —CH=CH— |
| 142 | 2-OCH₃—C₆H₄—CH(OH) | —CH=CH— |
| 143 | 4-OCH₃—C₆H₄—CH(OH) | —CH=CH— |
| 144 | 3,4-(OCH₃)₂—C₆H₃—CH(OH) | —CH=CH— |
| 145 | 2-OCH₃—C₆H₄—CH(OCH₃) | —CH=CH— |
| 146 | 4-OCH₃—C₆H₄—CH(OCH₃) | —CH=CH— |
| 147 | 3,4-(OCH₃)₂—C₆H₃—CH(OCH₃) | —CH=CH— |
| 148 | C₆H₅—CH₂CH₂ | —CH=CH— |
| 149 | C₆H₅—CH₂CH(CH₃) | —CH=CH— |
| 150 | 4-t-C₄H₉—C₆H₄—CH₂CH₂ | —CH=CH— |
| 151 | 4-t-C₄H₉—C₆H₄—CH₂CH(CH₃) | —CH=CH— |
| 152 | 2-Cl—C₆H₄—CH₂CH₂ | —CH=CH— |
| 153 | 3-Cl—C₆H₄—CH₂CH₂ | —CH=CH— |
| 154 | 4-Cl—C₆H₄—CH₂CH₂ | —CH=CH— |
| 155 | C₆H₅—CH=CH | —CH=CH— |
| 156 | 2-Cl—C₆H₄—CH=CH | —CH=CH— |
| 157 | 3-Cl—C₆H₄—CH=CH | —CH=CH— |
| 158 | 4-Cl—C₆H₄—CH=CH | —CH=CH— |
| 159 | 2,4-Cl₂—C₆H₃—CH=CH | —CH=CH— |
| 160 | 2-F—C₆H₄—CH=CH | —CH=CH— |
| 161 | 4-F—C₆H₄—CH=CH | —CH=CH— |
| 162 | 2-CH₃—C₆H₄—CH=CH | —CH=CH— |
| 163 | 4-CH₃—C₆H₄—CH=CH | —CH=CH— |
| 164 | 4-t-C₄H₉—C₆H₄—CH=CH | —CH=CH— |
| 165 | 2-OCH₃—C₆H₄—CH=CH | —CH=CH— |
| 166 | 4-OCH₃—C₆H₄—CH=CH | —CH=CH— |
| 167 | 4-phenoxy-C₆H₄—CH=CH | —CH=CH— |
| 168 | C₆H₅—(CH₂)₃ | —CH=CH— |
| 169 | C₆H₅—CH₂CH(CH₃)CH₂ | —CH=CH— |
| 170 | C₆H₅—(CH₂)₄ | —CH=CH— |
| 171 | C₆H₅—(CH₂)₅ | —CH=CH— |
| 172 | C₆H₅—(CH₂)₆ | —CH=CH— |
| 173 | 4-t-C₄H₉—C₆H₄—CH₂CH(CH₃)CH₂ | —CH=CH— |
| 174 | H | —CH₂CH₂— |
| 175 | CH₃ | —CH₂CH₂— |
| 176 | C₂H₅ | —CH₂CH₂— |
| 177 | n-C₃H₇ | —CH₂CH₂— |
| 178 | iso-C₃H₇ | —CH₂CH₂— |
| 179 | n-C₄H₉ | —CH₂CH₂— |
| 180 | (CH₃)₂CHCH₂ | —CH₂CH₂— |
| 181 | CH₃CH₂CH(CH₃) | —CH₂CH₂— |
| 182 | tert.C₄H₉ | —CH₂CH₂— |
| 183 | CH₃CH₂C(CH₃)₂ | —CH₂CH₂— |
| 184 | (CH₃)₃CCH₂ | —CH₂CH₂— |
| 185 | (CH₃)₂CHCH₂CH₂ | —CH₂CH₂— |
| 186 | CH₃CH₂CH₂CH(C₂H₅) | —CH₂CH₂— |
| 187 | n-C₅H₁₁ | —CH₂CH₂— |
| 188 | n-C₆H₁₃ | —CH₂CH₂— |
| 189 | n-C₇H₁₅ | —CH₂CH₂— |
| 190 | n-C₈H₁₇ | —CH₂CH₂— |
| 191 | n-C₉H₁₉ | —CH₂CH₂— |
| 192 | n-C₁₀H₂₁ | —CH₂CH₂— |
| 193 | n-C₁₅H₃₁ | —CH₂CH₂— |
| 194 | n-C₁₇H₃₅ | —CH₂CH₂— |
| 195 | CH₂=CH | —CH₂CH₂— |
| 196 | CH₂=C(CH₃) | —CH₂CH₂— |
| 197 | CH₃CH=CH | —CH₂CH₂— |
| 198 | CH₃CH=C(CH₃) | —CH₂CH₂— |
| 199 | (CH₃)₂C=CH | —CH₂CH₂— |
| 200 | CH₂=CHCH₂ | —CH₂CH₂— |
| 201 | CH₃CH=CHCH₂ | —CH₂CH₂— |
| 202 | (CH₃)₂C=CHCH₂ | —CH₂CH₂— |
| 203 | CH₃CH=CH—CH=CH | —CH₂CH₂— |
| 204 | (CH₃)₂C=CHCH₂CH₂C(CH₃)=CH | —CH₂CH₂— |
| 205 | (CH₃)₂CHCH₂CH₂CH₂CH(CH₃)CH₂ | —CH₂CH₂— |
| 206 | (CH₃)₂CHCH₂CH₂CH(CH₃)CH₂ | —CH₂CH₂— |
| 207 | HC≡C | —CH₂CH₂— |
| 208 | C₆H₅—C≡C | —CH₂CH₂— |
| 209 | CH₃OCH₂ | —CH₂CH₂— |
| 210 | C₂H₅OCH₂ | —CH₂CH₂— |
| 211 | CH₃CH(OCH₃) | —CH₂CH₂— |
| 212 | CN—CH₂ | —CH₂CH₂— |
| 213 | cyclopropyl | —CH₂CH₂— |
| 214 | cyclobutyl | —CH₂CH₂— |

-continued

| | | |
|---|---|---|
| 215 | cyclopentyl | —CH$_2$CH$_2$— |
| 216 | cyclohexyl | —CH$_2$CH$_2$— |
| 217 | 1-methylcyclopropyl | —CH$_2$CH$_2$— |
| 218 | 2,2-dichloro-1-methyl-cyclopropyl | —CH$_2$CH$_2$— |
| 219 | 2,2-dichloro-3,3-dimethyl-cyclopropyl | —CH$_2$CH$_2$— |
| 220 | 2,2,3,3-tetramethylcyclopropyl | —CH$_2$CH$_2$— |
| 221 | 2-(2'-methyl-1'-propenyl-)-3,3dimethylcyclopropyl | —CH$_2$CH$_2$— |
| 222 | 2-(2',2'-difluorovinyl)-3,3-dimethylcyclopropyl | —CH$_2$CH$_2$— |
| 223 | 2-(2',2'-dichlorovinyl)-3,3-dimethylcyclopropyl | —CH$_2$CH$_2$— |
| 224 | 2-(2',2'-dibromovinyl)-3,3-dimethylcyclopropyl | —CH$_2$CH$_2$— |
| 225 | 2-phenylcyclopropyl | —CH$_2$CH$_2$— |
| 226 | 2-(4'-chlorophenyl)cyclopropyl | —CH$_2$CH$_2$— |
| 227 | 2,2-dichloro-3-phenylcyclopropyl | —CH$_2$CH$_2$— |
| 228 | 2-carbomethoxy-cyclopropyl | —CH$_2$CH$_2$— |
| 229 | ClCH$_2$ | —CH$_2$CH$_2$— |
| 230 | Cl$_2$CH | —CH$_2$CH$_2$— |
| 231 | Cl$_3$C | —CH$_2$CH$_2$— |
| 232 | BrCH$_2$ | —CH$_2$CH$_2$— |
| 233 | CF$_3$ | —CH$_2$CH$_2$— |
| 234 | CH$_3$CH(Cl) | —CH$_2$CH$_2$— |
| 235 | C$_6$H$_5$ (=phenyl) | —CH$_2$CH$_2$— |
| 236 | 2-CH$_3$—C$_6$H$_4$ | —CH$_2$CH$_2$— |
| 237 | 3-CH$_3$—C$_6$H$_4$ | —CH$_2$CH$_2$— |
| 238 | 4-CH$_3$—C$_6$H$_4$ | —CH$_2$CH$_2$— |
| 239 | 2,3-(CH$_3$)$_2$—C$_6$H$_3$ | —CH$_2$CH$_2$— |
| 240 | 2,4-(CH$_3$)$_2$—C$_6$H$_3$ | —CH$_2$CH$_2$— |
| 241 | 2,6-(CH$_3$)$_2$—C$_6$H$_3$ | —CH$_2$CH$_2$— |
| 242 | 3,4-(CH$_3$)$_2$—C$_6$H$_3$ | —CH$_2$CH$_2$— |
| 243 | 3,5-(CH$_3$)$_2$—C$_6$H$_3$ | —CH$_2$CH$_2$— |
| 244 | 2,4,6-(CH$_3$)$_2$—C$_6$H$_2$ | —CH$_2$CH$_2$— |
| 245 | 4-t-C$_4$H$_9$—C$_6$H$_4$ | —CH$_2$CH$_2$— |
| 246 | 2-C$_6$H$_5$—C$_6$H$_4$ | —CH$_2$CH$_2$— |
| 247 | 4-C$_6$H$_5$—C$_6$H$_4$ | —CH$_2$CH$_2$— |
| 248 | 2-Cl—C$_6$H$_4$ | —CH$_2$CH$_2$— |
| 249 | 3-Cl—C$_6$H$_4$ | —CH$_2$CH$_2$— |
| 250 | 4-Cl—C$_6$H$_4$ | —CH$_2$CH$_2$— |
| 251 | 2,4-Cl$_2$—C$_6$H$_3$ | —CH$_2$CH$_2$— |
| 252 | 2,5-Cl$_2$—C$_6$H$_3$ | —CH$_2$CH$_2$— |
| 253 | 2,6-Cl$_2$—C$_6$H$_3$ | —CH$_2$CH$_2$— |
| 254 | 3,4-Cl$_2$—C$_6$H$_3$ | —CH$_2$CH$_2$— |
| 255 | 3,5-Cl$_2$—C$_6$H$_3$ | —CH$_2$CH$_2$— |
| 256 | 2,4,5-Cl$_3$—C$_6$H$_2$ | —CH$_2$CH$_2$— |
| 257 | 2,3,4,5,6-Cl$_5$—C$_6$ | —CH$_2$CH$_2$— |
| 258 | 6-F,2-Cl—C$_6$H$_3$ | —CH$_2$CH$_2$— |
| 260 | 2-F—C$_6$H$_4$ | —CH$_2$CH$_2$— |
| 261 | 3-F—C$_6$H$_4$ | —CH$_2$CH$_2$— |
| 262 | 4-F—C$_6$H$_4$ | —CH$_2$CH$_2$— |
| 263 | 2,4-F$_2$—C$_6$H$_3$ | —CH$_2$CH$_2$— |
| 264 | 2,6-F$_2$—C$_6$H$_3$ | —CH$_2$CH$_2$— |
| 265 | 2,3,4,5,6-F$_5$—C$_6$ | —CH$_2$CH$_2$— |
| 266 | 2-Br—C$_6$H$_4$ | —CH$_2$CH$_2$— |
| 267 | 3-Br—C$_6$H$_4$ | —CH$_2$CH$_2$— |
| 268 | 4-Br—C$_6$H$_4$ | —CH$_2$CH$_2$— |
| 269 | 2-CF$_3$—C$_6$H$_4$ | —CH$_2$CH$_2$— |
| 270 | 3-CF$_3$—C$_6$H$_4$ | —CH$_2$CH$_2$— |
| 271 | 4-CF$_3$—C$_6$H$_4$ | —CH$_2$CH$_2$— |
| 272 | 2-OCH$_3$—C$_6$H$_4$ | —CH$_2$CH$_2$— |
| 273 | 3-OCH$_3$—C$_6$H$_4$ | —CH$_2$CH$_2$— |
| 277 | 4-t-C$_4$H$_9$O—C$_6$H$_4$ | —CH$_2$CH$_2$— |
| 278 | 2-phenoxy-C$_6$H$_4$ | —CH$_2$CH$_2$— |
| 279 | 3-phenoxy-C$_6$H$_4$ | —CH$_2$CH$_2$— |
| 280 | 4-phenoxy-C$_6$H$_4$ | —CH$_2$CH$_2$— |
| 281 | C$_6$H$_5$—CH$_2$ | —CH$_2$CH$_2$— |
| 282 | 2-F—C$_6$H$_4$—CH$_2$ | —CH$_2$CH$_2$— |
| 283 | 3-F—C$_6$H$_4$—CH$_2$ | —CH$_2$CH$_2$— |
| 284 | 4-F—C$_6$H$_4$—CH$_2$ | —CH$_2$CH$_2$— |
| 285 | 2-Cl—C$_6$H$_4$—CH$_2$ | —CH$_2$CH$_2$— |
| 286 | 3-Cl—C$_6$H$_4$—CH$_2$ | —CH$_2$CH$_2$— |
| 287 | 4-Cl—C$_6$H$_4$—CH$_2$ | —CH$_2$CH$_2$— |
| 288 | 2-Cl,6F—C$_6$H$_3$—CH$_2$ | —CH$_2$CH$_2$— |
| 289 | 2,4-Cl$_2$—C$_6$H$_3$—CH$_2$ | —CH$_2$CH$_2$— |
| 290 | 2,6-Cl$_2$—C$_6$H$_3$—CH$_2$ | —CH$_2$CH$_2$— |
| 291 | 3,5-Cl$_2$—C$_6$H$_3$—CH$_2$ | —CH$_2$CH$_2$— |
| 292 | 2,4,6-Cl$_3$—C$_6$H$_2$—CH$_2$ | —CH$_2$CH$_2$— |
| 293 | 2-CH$_3$—C$_6$H$_4$—CH$_2$ | —CH$_2$CH$_2$— |
| 294 | 3-CH$_3$—C$_6$H$_4$—CH$_2$ | —CH$_2$CH$_2$— |
| 295 | 4-CH$_3$—C$_6$H$_4$—CH$_2$ | —CH$_2$CH$_2$— |
| 296 | 4-t-C$_4$H$_9$—C$_6$H$_4$—CH$_2$ | —CH$_2$CH$_2$— |
| 297 | 2,4-(CH$_3$)$_2$—C$_6$H$_3$—CH$_2$ | —CH$_2$CH$_2$— |
| 298 | 2,6-(CH$_3$)$_2$—C$_6$H$_3$—CH$_2$ | —CH$_2$CH$_2$— |
| 299 | 2,4,6-(CH$_3$)$_3$—C$_6$H$_2$—CH$_2$ | —CH$_2$CH$_2$— |
| 300 | 2-OCH$_3$—C$_6$H$_4$—CH$_2$ | —CH$_2$CH$_2$— |

-continued

| | | |
|---|---|---|
| 301 | 3-OCH$_3$—C$_6$H$_4$—CH$_2$ | —CH$_2$CH$_2$— |
| 302 | 4-OCH$_3$—C$_6$H$_4$—CH$_2$ | —CH$_2$CH$_2$— |
| 302 | 2-CF$_3$—C$_6$H$_4$—CH$_2$ | —CH$_2$CH$_2$— |
| 303 | 3-CF$_3$—C$_6$H$_4$—CH$_2$ | —CH$_2$CH$_2$— |
| 304 | 4-CF$_3$—C$_6$H$_4$—CH$_2$ | —CH$_2$CH$_2$— |
| 305 | 4-O-t-C$_4$H$_9$—C$_6$H$_4$—CH$_2$ | —CH$_2$CH$_2$— |
| 306 | 4-O—C$_6$H$_5$—C$_6$H$_4$—CH$_2$ | —CH$_2$CH$_2$— |
| 307 | 4-C$_6$H$_5$—C$_6$H$_4$—CH$_2$ | —CH$_2$CH$_2$— |
| 308 | 2-Br—C$_6$H$_4$—CH$_2$ | —CH$_2$CH$_2$— |
| 309 | 3-Br—C$_6$H$_4$—CH$_2$ | —CH$_2$CH$_2$— |
| 310 | 4-Br—C$_6$H$_4$—CH$_2$ | —CH$_2$CH$_2$— |
| 311 | C$_6$H$_5$—CH(CH$_3$) | —CH$_2$CH$_2$— |
| 312 | C$_6$H$_5$—CH(C$_2$H$_5$) | —CH$_2$CH$_2$— |
| 313 | C$_6$H$_5$—CH(iso-C$_3$H$_7$) | —CH$_2$CH$_2$— |
| 314 | C$_6$H$_5$—CH(OH) | —CH$_2$CH$_2$— |
| 315 | 2-OCH$_3$—C$_6$H$_4$—CH(OH) | —CH$_2$CH$_2$— |
| 316 | 4-OCH$_3$—C$_6$H$_4$—CH(OH) | —CH$_2$CH$_2$— |
| 317 | 3,4-(OCH$_3$)$_2$—C$_6$H$_3$—CH(OH) | —CH$_2$CH$_2$— |
| 318 | 2-OCH$_3$—C$_6$H$_4$—CH(OCH$_3$) | —CH$_2$CH$_2$— |
| 319 | 4-OCH$_3$—C$_6$H$_4$—CH(OCH$_3$) | —CH$_2$CH$_2$— |
| 320 | 3,4-(OCH$_3$)$_2$—C$_6$H$_3$—CH(OCH$_3$) | —CH$_2$CH$_2$— |
| 321 | C$_6$H$_5$—CH$_2$CH$_2$ | —CH$_2$CH$_2$— |
| 322 | C$_6$H$_5$—CH$_2$CH(CH$_3$) | —CH$_2$CH$_2$— |
| 323 | 4-t-C$_4$H$_9$—C$_6$H$_4$—CH$_2$CH$_2$ | —CH$_2$CH$_2$— |
| 324 | 4-t-C$_4$H$_9$—C$_6$H$_4$—CH$_2$CH(CH$_3$) | —CH$_2$CH$_2$— |
| 325 | 2-Cl-C$_6$H$_4$—CH$_2$CH$_2$ | —CH$_2$CH$_2$— |
| 326 | 3-Cl-C$_6$H$_4$—CH$_2$CH$_2$ | —CH$_2$CH$_2$— |
| 327 | 4-Cl—C$_6$H$_4$—CH$_2$CH$_2$ | —CH$_2$CH$_2$— |
| 328 | C$_6$H$_5$—CH=CH | —CH$_2$CH$_2$— |
| 329 | 2-Cl—C$_6$H$_4$—CH=CH | —CH$_2$CH$_2$— |
| 330 | 3-Cl—C$_6$H$_4$—CH=CH | —CH$_2$CH$_2$— |
| 331 | 4-Cl—C$_6$H$_4$—CH=CH | —CH$_2$CH$_2$— |
| 332 | 2,4-Cl$_2$—C$_6$H$_3$—CH=CH | —CH$_2$CH$_2$— |
| 333 | 2-F—C$_6$H$_4$—CH=CH | —CH$_2$CH$_2$— |
| 334 | 4-F—C$_6$H$_4$—CH=CH | —CH$_2$CH$_2$— |
| 335 | 2-CH$_3$—C$_6$H$_4$—CH=CH | —CH$_2$CH$_2$— |
| 336 | 4-CH$_3$—C$_6$H$_4$—CH=CH | —CH$_2$CH$_2$— |
| 337 | 4-t-C$_4$H$_9$—C$_6$H$_4$—CH=CH | —CH$_2$CH$_2$— |
| 338 | 2-OCH$_3$—C$_6$H$_4$—CH=CH | —CH$_2$CH$_2$— |
| 339 | 4-OCH$_3$—C$_6$H$_4$—CH=CH | —CH$_2$CH$_2$— |
| 340 | 4-phenoxy-C$_6$H$_4$—CH=CH | —CH$_2$CH$_2$— |
| 341 | C$_6$H$_5$—(CH$_2$)$_3$ | —CH$_2$CH$_2$— |
| 342 | C$_6$H$_5$—CH$_2$CH(CH$_3$)CH$_2$ | —CH$_2$CH$_2$— |
| 343 | C$_6$H$_5$—(CH$_2$)$_4$ | —CH$_2$CH$_2$— |
| 344 | C$_6$H$_5$—(CH$_2$)$_5$ | —CH$_2$CH$_2$— |
| 345 | C$_6$H$_5$—(CH$_2$)$_6$ | —CH$_2$CH$_2$— |
| 346 | 4-t-C$_4$H$_9$—C$_6$H$_4$—CH$_2$CH(CH$_3$)CH$_2$ | —CH$_2$CH$_2$— |
| 347 | C$_6$H$_5$O | —CH$_2$CH$_2$— |
| 348 | 2-Cl—C$_6$H$_4$O | —CH$_2$CH$_2$— |
| 349 | 3-Cl—C$_6$H$_4$O | —CH$_2$CH$_2$— |
| 350 | 4-Cl—C$_6$H$_4$O | —CH$_2$CH$_2$— |
| 351 | 2-CH$_3$—C$_6$H$_4$O | —CH$_2$CH$_2$— |
| 352 | 4-CH$_3$—C$_6$H$_4$O | —CH$_2$CH$_2$— |
| 353 | 2-OCH$_3$—C$_6$H$_4$O | —CH$_2$CH$_2$— |
| 354 | 4-OCH$_3$—C$_6$H$_4$O | —CH$_2$CH$_2$— |
| 355 | 2-CF$_3$—C$_6$H$_4$O | —CH$_2$CH$_2$— |
| 356 | 4-CF$_3$—C$_6$H$_4$O | —CH$_2$CH$_2$— |
| 357 | C$_6$H$_5$OCH$_2$ | —CH$_2$CH$_2$— |
| 358 | 2-Cl—C$_6$H$_4$OCH$_2$ | —CH$_2$CH$_2$— |
| 359 | 4-Cl—C$_6$H$_4$OCH$_2$ | —CH$_2$CH$_2$— |
| 360 | 2-CH$_3$—C$_6$H$_4$OCH$_2$ | —CH$_2$CH$_2$— |
| 361 | 4-CH$_3$—C$_6$H$_4$OCH$_2$ | —CH$_2$CH$_2$— |
| 362 | 2-OCH$_3$—C$_6$H$_4$OCH$_2$ | —CH$_2$CH$_2$— |
| 363 | 4-OCH$_3$—C$_6$H$_4$OCH$_2$ | —CH$_2$CH$_2$— |
| 364 | 4-t-C$_4$H$_9$—C$_6$H$_4$OCH$_2$ | —CH$_2$CH$_2$— |
| 365 | C$_6$H$_5$OCH$_2$CH$_2$ | —CH$_2$CH$_2$— |
| 366 | 2-Cl—C$_6$H$_4$OCH$_2$CH$_2$ | —CH$_2$CH$_2$— |
| 367 | 4-Cl—C$_6$H$_4$OCH$_2$CH$_2$ | —CH$_2$CH$_2$— |
| 368 | 4-F—C$_6$H$_4$OCH$_2$CH$_2$ | —CH$_2$CH$_2$— |
| 369 | 2-CH$_3$—C$_6$H$_4$OCH$_2$CH$_2$ | —CH$_2$CH$_2$— |
| 370 | 4-CH$_3$—C$_6$H$_4$OCH$_2$CH$_2$ | —CH$_2$CH$_2$— |
| 371 | 2-OCH$_3$—C$_6$H$_4$OCH$_2$CH$_2$ | —CH$_2$CH$_2$— |
| 372 | 4-OCH$_3$—C$_6$H$_4$OCH$_2$CH$_2$ | —CH$_2$CH$_2$— |
| 373 | 4-t-C$_4$H$_9$—C$_6$H$_4$—OCH$_2$CH$_2$ | —CH$_2$CH$_2$— |
| 374 | C$_6$H$_5$O(CH$_2$)$_3$ | —CH$_2$CH$_2$— |
| 375 | 2-Cl—C$_6$H$_4$O(CH$_2$)$_3$ | —CH$_2$CH$_2$— |
| 376 | 4-Cl—C$_6$H$_4$O(CH$_2$)$_3$ | —CH$_2$CH$_2$— |
| 377 | C$_6$H$_5$O(CH$_2$)$_4$ | —CH$_2$CH$_2$— |
| 378 | 2-Cl—C$_6$H$_4$—O(CH$_2$)$_4$ | —CH$_2$CH$_2$— |
| 379 | 4-Cl—C$_6$H$_4$—O(CH$_2$)$_4$ | —CH$_2$CH$_2$— |
| 380 | C$_6$H$_5$O(CH$_2$)$_5$ | —CH$_2$CH$_2$— |
| 381 | 2-Cl—C$_6$H$_4$O(CH$_2$)$_5$ | —CH$_2$CH$_2$— |

-continued

| | | | |
|---|---|---|---|
| 382 | 4-Cl—C$_6$H$_4$O(CH$_2$)$_5$ | —CH$_2$CH$_2$— | |
| 383 | C$_6$H$_5$O(CH$_2$)$_6$ | —CH$_2$CH$_2$— | |
| 384 | C$_6$H$_5$OCH$_2$CH$_2$O | —CH$_2$CH$_2$— | |
| 385 | H | —CH$_2$O— | |
| 386 | CH$_3$ | —CH$_2$O— | |
| 387 | C$_2$H$_5$ | —CH$_2$O— | |
| 388 | n-C$_3$H$_7$ | —CH$_2$O— | |
| 389 | iso-C$_3$H$_7$ | —CH$_2$O— | |
| 390 | n-C$_4$H$_9$ | —CH$_2$O— | |
| 391 | (CH$_3$)$_2$CHCH$_2$ | —CH$_2$O— | |
| 392 | CH$_3$CH$_2$CH(CH$_3$) | —CH$_2$O— | |
| 393 | tert.C$_4$H$_9$ | —CH$_2$O— | |
| 394 | CH$_3$CH$_2$C(CH$_3$)$_2$ | —CH$_2$O— | |
| 395 | (CH$_3$)$_3$CCH$_2$ | —CH$_2$O— | |
| 396 | (CH$_3$)$_2$CHCH$_2$CH$_2$ | —CH$_2$O— | |
| 397 | CH$_3$CH$_2$CH$_2$CH(C$_2$H$_5$) | —CH$_2$O— | |
| 398 | n-C$_5$H$_{11}$ | —CH$_2$O— | |
| 399 | n-C$_6$H$_{13}$ | —CH$_2$O— | |
| 400 | n-C$_7$H$_{15}$ | —CH$_2$O— | |
| 401 | n-C$_8$H$_{17}$ | —CH$_2$O— | |
| 402 | n-C$_9$H$_{19}$ | —CH$_2$O— | |
| 403 | n-C$_{10}$H$_{21}$ | —CH$_2$O— | |
| 404 | n-C$_{15}$H$_{31}$ | —CH$_2$O— | |
| 405 | n-C$_{17}$H$_{35}$ | —CH$_2$O— | |
| 406 | CH$_2$=CH | —CH$_2$O— | |
| 407 | CH$_2$=C(CH$_3$) | —CH$_2$O— | |
| 408 | CH$_3$CH=CH | —CH$_2$O— | |
| 409 | CH$_3$CH=C(CH$_3$) | —CH$_2$O— | |
| 410 | (CH$_3$)$_2$C=CH | —CH$_2$O— | |
| 411 | CH$_2$=CHCH$_2$ | —CH$_2$O— | |
| 412 | CH$_3$CH=CHCH$_2$ | —CH$_2$O— | |
| 413 | (CH$_3$)$_2$C=CHCH$_2$ | —CH$_2$O— | |
| 414 | CH$_3$CH=CH—CH=CH | —CH$_2$O— | |
| 415 | (CH$_3$)$_2$C=CHCH$_2$CH$_2$C(CH$_3$)=CH | —CH$_2$O— | |
| 416 | (CH$_3$)$_2$CHCH$_2$CH$_2$CH$_2$CH(CH$_3$)CH$_2$ | —CH$_2$O— | |
| 417 | (CH$_3$)$_2$C=CHCH$_2$CH$_2$CH(CH$_3$)CH$_2$ | —CH$_2$O— | |
| 418 | HC≡C | —CH$_2$O— | |
| 419 | C$_6$H$_5$—C≡C | —CH$_2$O— | |
| 420 | CH$_3$OCH$_2$ | —CH$_2$O— | |
| 421 | C$_2$H$_5$OCH$_2$ | —CH$_2$O— | |
| 422 | CH$_3$CH(OCH$_3$) | —CH$_2$O— | |
| 423 | CN—CH$_2$ | —CH$_2$O— | |
| 424 | cyclopropyl | —CH$_2$O— | |
| 425 | cyclobutyl | —CH$_2$O— | |
| 426 | cyclopentyl | —CH$_2$O— | |
| 427 | cyclohexyl | —CH$_2$O— | |
| 428 | 1-methylcyclopropyl | —CH$_2$O— | |
| 429 | 2,2-dichloro-1-methyl-cyclopropyl | —CH$_2$O— | |
| 430 | 2,2-dichloro-3,3-dimethyl-cyclopropyl | —CH$_2$O— | |
| 431 | 2,2,3,3-tetramethylcyclopropyl | —CH$_2$O— | |
| 432 | 2-(2'-methyl-1'-propenyl-)-3,3-dimethylcyclopropyl | —CH$_2$O— | |
| 433 | 2-(2',2'-difluorovinyl)-3,3-dimethylcyclopropyl | —CH$_2$O— | |
| 434 | 2-(2',2'-dichlorovinyl)-3,3-dimethylcyclopropyl | —CH$_2$O— | |
| 435 | 2-(2',2'-dibromovinyl)-3,3-dimethylcyclopropyl | —CH$_2$O— | |
| 436 | 2-phenylcyclopropyl | —CH$_2$O— | |
| 437 | 2-(4'-chlorophenyl)cyclopropyl | —CH$_2$O— | |
| 438 | 2,2-dichloro-3-phenylcyclopropyl | —CH$_2$O— | |
| 439 | 2-carbomethoxy-cyclopropyl | —CH$_2$O— | |
| 440 | Cl$_2$CH | —CH$_2$O— | |
| 441 | Cl$_2$CH | —CH$_2$O— | |
| 442 | Cl$_3$C | —CH$_2$O— | |
| 443 | BrCH$_2$ | —CH$_2$O— | |
| 444 | CF$_3$ | —CH$_2$O— | |
| 445 | CH$_3$CH(Cl) | —CH$_2$O— | |
| 446 | C$_6$H$_5$ (=phenyl) | —CH$_2$O— | oil; IR (film): 1727,1602,1495,1451,1276, 1242,1208,753,735,696 cm$^{-1}$ |
| 447 | 2-CH$_3$—C$_6$H$_4$ | —CH$_2$O— | |
| 448 | 3-CH$_3$—C$_6$H$_4$ | —CH$_2$O— | oil; IR (film): 1738,1602,1495,1242,1160 1018,753 cm$^{-1}$ |
| 449 | 4-CH$_3$—C$_6$H$_4$ | —CH$_2$O— | |
| 450 | 2,3-(CH$_3$)$_2$—C$_6$H$_3$ | —CH$_2$O— | |
| 451 | 2,4-(CH$_3$)$_2$—C$_6$H$_3$ | —CH$_2$O— | |
| 452 | 2,6-(CH$_3$)$_2$—C$_6$H$_3$ | —CH$_2$O— | |
| 453 | 3,4-(CH$_3$)$_2$—C$_6$H$_3$ | —CH$_2$O— | |
| 454 | 3,5-(CH$_3$)$_2$—C$_6$H$_3$ | —CH$_2$O— | |
| 455 | 2,4,6-(CH$_3$)$_2$—C$_6$H$_2$ | —CH$_2$O— | |
| 456 | 4-t-C$_4$H$_9$—C$_6$H$_4$ | —CH$_2$O— | |
| 457 | 2-C$_6$H$_5$—C$_6$H$_4$ | —CH$_2$O— | |
| 458 | 4-C$_6$H$_5$—C$_6$H$_4$ | —CH$_2$O— | |
| 459 | 2-Cl—C$_6$H$_4$ | —CH$_2$O— | |

-continued

| | | | |
|---|---|---|---|
| 460 | 3-Cl—C$_6$H$_4$ | —CH$_2$O— | oil; IR (film): 1726,1491 1451,1210,753 cm$^{-1}$ |
| 461 | 4-Cl—C$_6$H$_4$ | —CH$_2$O— | |
| 462 | 2,4-Cl$_2$—C$_6$H$_3$ | —CH$_2$O— | |
| 463 | 2,5-Cl$_2$—C$_6$H$_3$ | —CH$_2$O— | |
| 464 | 2,6-Cl$_2$—C$_6$H$_3$ | —CH$_2$O— | |
| 465 | 3,4-Cl$_2$—C$_6$H$_3$ | —CH$_2$O— | |
| 466 | 3,5-Cl$_2$—C$_6$H$_3$ | —CH$_2$O— | |
| 467 | 2,4,5-Cl$_3$—C$_6$H$_2$ | —CH$_2$O— | |
| 468 | 2,3,4,5,6-Cl$_5$—C$_6$ | —CH$_2$O— | |
| 469 | 6-F,2-Cl—C$_6$H$_3$ | —CH$_2$O— | |
| 470 | 2-F—C$_6$H$_4$ | —CH$_2$O— | |
| 471 | 3-F—C$_6$H$_4$ | —CH$_2$O— | |
| 472 | 2,4-F$_2$—C$_6$H$_3$ | —CH$_2$O— | |
| 473 | 2,6-F$_2$—G$_6$H$_3$ | —CH$_2$O— | |
| 474 | 2,6-F$_2$—C$_6$H$_3$ | —CH$_2$O— | |
| 475 | 2,3,4,5,6-E$_5$—C$_6$ | —CH$_2$O— | |
| 476 | 2-Br—C$_6$H$_4$ | —CH$_2$O— | |
| 477 | 3-Br—C$_6$H$_4$ | —CH$_2$O— | |
| 478 | 4-Br—C$_6$H$_4$ | —CH$_2$O— | |
| 479 | 2-CF$_3$—C$_6$H$_4$ | —CH$_2$O— | |
| 480 | 3-CF$_3$—C$_6$H$_4$ | —CH$_2$O— | |
| 481 | 4-CF$_3$—C$_6$H$_4$ | —CH$_2$O— | |
| 482 | 2-OCH$_3$—C$_6$H$_4$ | —CH$_2$O— | |
| 483 | 3-OCH$_3$—C$_6$H$_4$ | —CH$_2$O— | |
| 484 | 4-OCH$_3$—C$_6$H$_4$ | —CH$_2$O— | |
| 485 | 3,4-(OCH$_3$)$_2$—C$_6$H$_3$ | —CH$_2$O— | |
| 486 | 3,4,5-(OCH$_3$)$_3$—C$_6$H$_2$ | —CH$_2$O— | |
| 487 | 4-t-C$_4$H$_9$O—C$_6$H$_4$ | —CH$_2$O— | |
| 488 | 2-phenoxy-C$_6$H$_4$ | —CH$_2$O— | |
| 489 | 3-phenoxy-C$_6$H$_4$ | —CH$_2$O— | |
| 490 | 4-phenoxy-C$_6$H$_4$ | —CH$_2$O— | |
| 491 | C$_6$H$_5$—CH$_2$ | —CH$_2$O— | |
| 492 | 2-F—C$_6$H$_4$—CH$_2$ | —CH$_2$O— | |
| 493 | 3-F—C$_6$H$_4$—CH$_2$ | —CH$_2$O— | |
| 494 | 4-F—C$_6$H$_4$—CH$_2$ | —CH$_2$O— | |
| 495 | 2-Cl—C$_6$H$_4$—CH$_2$ | —CH$_2$O— | |
| 496 | 3-Cl—C$_6$H$_4$—CH$_2$ | —CH$_2$O— | |
| 497 | 4-Cl—C$_6$H$_4$—CH$_2$ | —CH$_2$O— | |
| 498 | 2-Cl,6F—C$_6$H$_3$—CH$_2$ | —CH$_2$O— | |
| 499 | 2,4-Cl$_2$—C$_6$H$_3$—CH$_2$ | —CH$_2$O— | |
| 500 | 2,6-Cl$_2$—C$_6$H$_3$—CH$_2$ | —CH$_2$O— | |
| 501 | 3,5-Cl$_2$—C$_6$H$_3$—CH$_2$ | —CH$_2$O— | |
| 502 | 2,4,6-Cl$_3$—C$_6$H$_2$—CH$_2$ | —CH$_2$O— | |
| 503 | 2-CH$_3$—C$_6$H$_4$—CH$_2$ | —CH$_2$O— | |
| 504 | 3-CH$_3$—C$_6$H$_4$—CH$_2$ | —CH$_2$O— | |
| 505 | 4-CH$_3$—C$_6$H$_4$—CH$_2$ | —CH$_2$O— | |
| 506 | 4-t-C$_4$H$_9$—C$_6$H$_4$—CH$_2$ | —CH$_2$O— | |
| 507 | 2,4-(CH$_3$)$_2$—C$_6$H$_3$—CH$_2$ | —CH$_2$O— | |
| 508 | 2,6-(CH$_3$)$_2$—C$_6$H$_3$—CH$_2$ | —CH$_2$O— | |
| 509 | 2,4,6-(CH$_3$)$_3$—C$_6$H$_2$—CH$_2$ | —CH$_2$O— | |
| 510 | 2-OCH$_3$—C$_6$H$_4$—CH$_2$ | —CH$_2$O— | |
| 511 | 3-OCH$_3$—C$_6$H$_4$—CH$_2$ | —CH$_2$O— | |
| 512 | 4-OCH$_3$—C$_6$H$_4$—CH$_2$ | —CH$_2$O— | |
| 513 | 2-CF$_3$—C$_6$H$_4$—CH$_2$ | —CH$_2$O— | |
| 514 | 3-CF$_3$—C$_6$H$_4$—CH$_2$ | —CH$_2$O— | |
| 515 | 4-CF$_3$—C$_6$H$_4$—CH$_2$ | —CH$_2$O— | |
| 516 | 4-O-t-C$_4$H$_9$—C$_6$H$_4$—CH$_2$ | —CH$_2$O— | |
| 517 | 4-O—C$_6$H$_5$—C$_6$H$_4$—CH$_2$ | —CH$_2$O— | |
| 518 | 4-C$_6$H$_5$—C$_6$H$_4$—CH$_2$ | —CH$_2$O— | |
| 519 | 2-Br—C$_6$H$_4$—CH$_2$ | —CH$_2$O— | |
| 520 | 3-Br—C$_6$H$_4$—CH$_2$ | —CH$_2$O— | |
| 521 | 4-Br—C$_6$H$_4$—CH$_2$ | —CH$_2$O— | |
| 522 | C$_6$H$_5$—CH(CH$_3$) | —CH$_2$O— | |
| 523 | C$_6$H$_5$—CH(C$_2$H$_5$) | —CH$_2$O— | |
| 524 | C$_6$H$_5$—CH(iso-C$_3$H$_7$) | —CH$_2$O— | |
| 525 | C$_6$H$_5$—CH(OH) | —CH$_2$O— | |
| 526 | 2-OCH$_3$—C$_6$H$_4$—CH(OH) | —CH$_2$O— | |
| 527 | 4-OCH$_3$—C$_6$H$_4$—CH(OH) | —CH$_2$O— | |
| 528 | 3,4-(OCH$_3$)$_2$—C$_6$H$_3$—CH(OH) | —CH$_2$O— | |
| 529 | 2-OCH$_3$—C$_6$H$_4$—CH(OCH$_3$) | —CH$_2$O— | |
| 530 | 4-OCH$_3$—C$_6$H$_4$—CH(OCH$_3$) | —CH$_2$O— | |
| 531 | 3,4-(OCH$_3$)$_2$—C$_6$H$_3$—CH(OCH$_3$) | —CH$_2$O— | |
| 532 | C$_6$H$_5$—CH$_2$CH$_2$ | —CH$_2$O— | |
| 533 | C$_6$H$_5$—CH$_2$CH(CH$_3$) | —CH$_2$O— | |
| 534 | 4-t-C$_4$H$_9$—C$_6$H$_4$—CH$_2$CH$_2$ | —CH$_2$O— | |
| 535 | 4-t-C$_4$H$_9$—C$_6$H$_4$—CH$_2$CH(CH$_3$) | —CH$_2$O— | |
| 536 | 2-Cl—C$_6$H$_4$—CH$_2$CH$_2$ | —CH$_2$O— | |
| 537 | 3-Cl—C$_6$H$_4$—CH$_2$CH$_2$ | —CH$_2$O— | |
| 538 | 4-Cl—C$_6$H$_4$—CH$_2$CH$_2$ | —CH$_2$O— | |
| 539 | C$_6$H$_5$—CH=CH | —CH$_2$O— | |
| 540 | 2-Cl—C$_6$H$_4$—CH=CH | —CH$_2$O— | |

-continued

| | | |
|---|---|---|
| 541 | 3-Cl—C₆H₄—CH=CH | —CH₂O— |
| 542 | 4-Cl—C₆H₄—CH=CH | —CH₂O— |
| 543 | 2,4-Cl₂—C₆H₃—CH=CH | —CH₂O— |
| 545 | 2-F—C₆H₄—CH=CH | —CH₂O— |
| 546 | 4-F—C₆H₄—CH=CH | —CH₂O— |
| 547 | 2-CH₃—C₆H₄—CH=CH | —CH₂O— |
| 548 | 4-CH₃—C₆H₄—CH=CH | —CH₂O— |
| 549 | 4-t-C₄H₉—C₆H₄—CH=CH | —CH₂O— |
| 550 | 2-OCH₃—C₆H₄—CH=CH | —CH₂O— |
| 551 | 4-OCH₃—C₆H₄—CH=CH | —CH₂O— |
| 552 | 4-phenoxy-C₆H₄—CH=CH | —CH₂O— |
| 553 | C₆H₅—(CH₂)₃ | —CH₂O— |
| 554 | C₆H₅—CH₂CH(CH₃)CH₂ | —CH₂O— |
| 555 | C₆H₅—(CH₂)₄ | —CH₂O— |
| 556 | C₆H₅—(CH₂)₅ | —CH₂O— |
| 557 | C₆H₅—(CH₂)₆ | —CH₂O— |
| 558 | 4-t-C₄H₉—C₆H₄—CH₂CH(CH₃)CH₂ | —CH₂O— |
| 559 | H | —OCH₂— |
| 560 | CH₃ | —OCH₂— |
| 561 | C₂H₅ | —OCH₂— |
| 562 | n-C₃H₇ | —OCH₂— |
| 563 | iso-C₃H₇ | —OCH₂— |
| 564 | n-C₄H₉ | —OCH₂— |
| 565 | (CH₃)₂CHCH₂ | —OCH₂— |
| 566 | CH₃CH₂CH(CH₃) | —OCH₂— |
| 567 | tert.C₄H₉ | —OCH₂— |
| 568 | CH₃CH₂C(CH₃)₂ | —OCH₂— |
| 569 | (CH₃)₃CCH₂ | —OCH₂— |
| 570 | (CH₃)₂CHCH₂CH₂ | —OCH₂— |
| 571 | CH₃CH₂CH₂CH(C₂H₅) | —OCH₂— |
| 572 | n-C₅H₁₁ | —OCH₂— |
| 573 | n-C₆H₁₃ | —OCH₂— |
| 574 | n-C₇H₁₅ | —OCH₂— |
| 575 | n-C₈H₁₇ | —OCH₂— |
| 576 | n-C₉H₁₉ | —OCH₂— |
| 577 | n-C₁₀H₂₁ | —OCH₂— |
| 578 | n-C₁₅H₃₁ | —OCH₂— |
| 579 | n-C₁₇H₃₅ | —OCH₂— |
| 580 | CH₂=CH | —OCH₂— |
| 581 | CH₂=C(CH₃) | —OCH₂— |
| 582 | CH₃CH=CH | —OCH₂— |
| 583 | CH₃CH=C(CH₃) | —OCH₂— |
| 584 | (CH₃)₂C=CH | —OCH₂— |
| 585 | CH₂=CHCH₂ | —OCH₂— |
| 586 | CH₃CH=CHCH₂ | —OCH₂— |
| 587 | (CH₃)₂C=CHCH₂ | —OCH₂— |
| 588 | CH₃CH=CH—CH=CH | —OCH₂— |
| 589 | (CH₃)₂C=CHCH₂CH₂C(CH₃)=CH | —OCH₂— |
| 590 | (CH₃)₂CHCH₂CH₂CH₂CH(CH₃)CH₂ | —OCH₂— |
| 591 | (CH₃)₂C=CHCH₂CH₂CH(CH₃)CH₂ | —OCH₂— |
| 592 | (CH₃)₂C=CHCH₂CH₂CH(CH₃)CH₂ | —OCH₂— |
| 593 | CH₃OCH₂ | —OCH₂— |
| 594 | C₂H₅OCH₂ | —OCH₂— |
| 595 | CH₃CH(OCH₃) | —OCH₂— |
| 596 | CN—CH₂ | —OCH₂— |
| 597 | cyclopropyl | —OCH₂— |
| 598 | cyclobutyl | —OCH₂— |
| 599 | cyclopentyl | —OCH₂— |
| 600 | cyclohexyl | —OCH₂— |
| 601 | 1-methylcyclopropyl | —OCH₂— |
| 602 | 2,2-dichloro-1-methyl-cyclopropyl | —OCH₂— |
| 603 | 2,2-dichloro-3,3-dimethyl-cyclopropyl | —OCH₂— |
| 604 | 2,2,3,3-tetramethylcyclopropyl | —OCH₂— |
| 605 | 2-(2'-methyl-1'-propenyl-)-3,3-dimethylcyclopropyl | —OCH₂— |
| 606 | 2-(2',2'-difluorovinyl)-3,3-dimethylcyclopropyl | —OCH₂— |
| 607 | 2-(2',2'-dichlorovinyl)-3,3-dimethylcyclopropyl | —OCH₂— |
| 608 | 2-(2',2'-dibromovinyl)-3,3-dimethylcyclopropyl | —OCH₂— |
| 609 | 2-phenylcyclopropyl | —OCH₂— |
| 610 | 2-(4'-chlorophenyl)cyclopropyl | —OCH₂— |
| 611 | 2,2-dichloro-3-phenylcyclopropyl | —OCH₂— |
| 612 | 2-carbomethoxy-cyclopropyl | —OCH₂— |
| 613 | Cl₂CH | —OCH₂— |
| 614 | Cl₂CH | —OCH₂— |
| 615 | Cl₃C | —OCH₂— |
| 616 | BrCH₂ | —OCH₂— |
| 617 | CF₃ | —OCH₂— |
| 618 | CH₃CH(Cl) | —OCH₂— |
| 619 | C₆H₅ (=phenyl) | —OCH₂— |

-continued

| | | |  |
|---|---|---|---|
| 620 | 2-CH₃—C₆H₄ | —OCH₂— | |
| 621 | 3-CH₃—C₆H₄ | —OCH₂— | |
| 622 | 4-CH₃—C₆H₄ | —OCH₂— | |
| 623 | 2,3-(CH₃)₂—C₆H₃ | —OCH₂— | |
| 624 | 2,4-(CH₃)₂—C₆H₃ | —OCH₂— | |
| 625 | 2,6-(CH₃)₂—C₆H₃ | —OCH₂— | |
| 626 | 3,4-(CH₃)₂—C₆H₃ | —OCH₂— | |
| 627 | 3,5-(CH₃)₂—C₆H₃ | —OCH₂— | |
| 628 | 2,4,6-(CH₃)₂—C₆H₂ | —OCH₂— | |
| 629 | 4-t-C₄H₉—C₆H₄ | —OCH₂— | |
| 630 | 2-C₆H₅—C₆H₄ | —OCH₂— | |
| 631 | 4-C₆H₅—C₆H₄ | —OCH₂— | |
| 632 | 2-Cl—C₆H₄ | —OCH₂— | oil; $^1$H-NMR (CDCl₃): $\delta$ = 3.75(3H), 5.03(2H), 5.83(2H), 6.58(1H), 6.90(1H), 7.0–7.6(8H) |
| 633 | 3-Cl—C₆H₄ | —OCH₂— | |
| 634 | 4-Cl—C₆H₄ | —OCH₂— | |
| 635 | 2,4-Cl₂—C₆H₃ | —OCH₂— | |
| 636 | 2,5-Cl₂—C₆H₃ | —OCH₂— | |
| 637 | 2,6-Cl₂—C₆H₃ | —OCH₂— | |
| 638 | 3,4-Cl₂—C₆H₃ | —OCH₂— | |
| 639 | 3,5-Cl₂—C₆H₃ | —OCH₂— | |
| 640 | 2,4,5-Cl₃—C₆H₂ | —OCH₂— | |
| 641 | 2,3,4,5,6-Cl₅—C₆ | —OCH₂— | |
| 642 | 6-F,2-Cl—C₆H₃ | —OCH₂— | |
| 643 | 2-F—C₆H₄ | —OCH₂— | |
| 644 | 3-F—C₆H₄ | —OCH₂— | |
| 645 | 4-F—C₆H₄ | —OCH₂— | |
| 646 | 2,4-F₂—C₆H₃ | —OCH₂— | |
| 647 | 2,6-F₂—C₆H₃ | —OCH₂— | |
| 648 | 2,3,4,5,6-F₅—C₆ | —OCH₂— | |
| 649 | 2-Br—C₆H₄ | —OCH₂— | oil; $^1$H-NMR (CDCl₃): $\delta$ = 3.77(3H), 5.03(2H), 5.83(2H), 6.60(1H), 6.83(2H), 7.1–7.7(6H) |
| 650 | 3-Br—C₆H₄ | —OCH₂— | |
| 651 | 4-Br—C₆H₄ | —OCH₂— | |
| 652 | 2-CF₃—C₆H₄ | —OCH₂— | |
| 653 | 3-CF₃—C₆H₄ | —OCH₂— | |
| 654 | 4-CF₃—C₆H₄ | —OCH₂— | |
| 655 | 2-OCH₃—C₆H₄ | —OCH₂— | |
| 656 | 3-OCH₃—C₆H₄ | —OCH₂— | |
| 657 | 4-OCH₃—C₆H₄ | —OCH₂— | |
| 658 | 3,4-(OCH₃)₂—C₆H₃ | —OCH₂— | |
| 659 | 3,4,5-(OCH₃)₃—C₆H₂ | —OCH₂— | |
| 660 | 4-t-C₄H₉O—C₆H₄ | —OCH₂— | |
| 661 | 2-phenoxy-C₆H₄ | —OCH₂— | |
| 662 | 3-phenoxy-C₆H₄ | —OCH₂— | |
| 663 | 4-phenoxy-C₆H₄ | —OCH₂— | |
| 664 | C₆H₅—CH₂ | —OCH₂— | |
| 665 | 2-F—C₆H₄—CH₂ | —OCH₂— | |
| 666 | 3-F—C₆H₄—CH₂ | —OCH₂— | |
| 667 | 4-F—C₆H₄—CH₂ | —OCH₂— | |
| 668 | 2-Cl—C₆H₄—CH₂ | —OCH₂— | |
| 669 | 3-Cl—C₆H₄—CH₂ | —OCH₂— | |
| 670 | 4-Cl—C₆H₄—CH₂ | —OCH₂— | |
| 671 | 2-Cl,6F—C₆H₃—CH₂ | —OCH₂— | |
| 672 | 2,4-Cl₂—C₆H₃—CH₂ | —OCH₂— | |
| 673 | 2,6-Cl₂—C₆H₃—CH₂ | —OCH₂— | |
| 674 | 3,5-Cl₂—C₆H₃—CH₂ | —OCH₂— | |
| 675 | 2,4,6-Cl₃—C₆H₂—CH₂ | —OCH₂— | |
| 676 | 2-CH₃—C₆H₄—CH₂ | —OCH₂— | |
| 677 | 3-CH₃—C₆H₄—CH₂ | —OCH₂— | |
| 678 | 4-CH₃—C₆H₄—CH₂ | —OCH₂— | |
| 679 | 4-t-C₄H₉—C₆H₄—CH₂ | —OCH₂— | |
| 680 | 2,4-(CH₃)₂—C₆H₃—CH₂ | —OCH₂— | |
| 681 | 2,6-(CH₃)₂—C₆H₃—CH₂ | —OCH₂— | |
| 682 | 2,4,6-(CH₃)₃—C₆H₂—CH₂ | —OCH₂— | |
| 683 | 2-OCH₃—C₆H₄—CH₂ | —OCH₂— | |
| 684 | 3-OCH₃—C₆H₄—CH₂ | —OCH₂— | |
| 685 | 4-OCH₃—C₆H₄—CH₂ | —OCH₂— | |
| 686 | 2-CF₃—C₆H₄—CH₂ | —OCH₂— | |
| 687 | 3-CF₃—C₆H₄—CH₂ | —OCH₂— | |
| 688 | 4-CF₃—C₆H₄—CH₂ | —OCH₂— | |
| 689 | 4-O-t-C₄H₉—C₆H₄—CH₂ | —OCH₂— | |
| 690 | 4-O—C₆H₅—C₆H₄—CH₂ | —OCH₂— | |
| 691 | 4-C₆H₅—CH₂ | —OCH₂— | |
| 692 | 2-Br—C₆H₄—CH₂ | —OCH₂— | |
| 693 | 3-Br—C₆H₄—CH₂ | —OCH₂— | |
| 694 | 4-Br—C₆H₄—CH₂ | —OCH₂— | |
| 695 | C₆H₅—CH(CH₃) | —OCH₂— | |

-continued

| | | | |
|---|---|---|---|
| 696 | $C_6H_5$—$CH(C_2H_5)$ | —$OCH_2$— | |
| 697 | $C_6H_5$—$CH(iso$-$C_3H)$ | —$OCH_2$— | |
| 698 | $C_6H_5$—$CH_2CH_2$ | —$OCH_2$— | |
| 699 | $C_6H_5$—$CH_2CH(CH_3)$ | —$OCH_3$— | |
| 700 | 4-t-$C_4H_9$—$C_6H_4$—$CH_2CH_2$ | —$OCH_2$— | |
| 701 | 4-t-$C_4H_9$—$C_6H_4$—$CH_2CH(CH_3)$ | —$OCH_2$— | |
| 702 | 2-Cl—$C_6H_4$—$CH_2CH_2$ | —$OCH_2$— | |
| 703 | 3-Cl—$C_6H_4$—$CH_2CH_2$ | —$OCH_2$— | |
| 704 | 4-Cl—$C_6H_4$—$CH_2CH_3$ | —$OCH_2$— | |
| 705 | $C_6H_5$—CH=CH | —$OCH_2$— | |
| 706 | $C_6H_5$—$(CH_2)_3$ | —$OCH_2$— | |
| 707 | $C_6H_5$—$CH_2CH(CH_3)CH_2$ | —$OCH_2$— | |
| 708 | $C_6H_5$—$(CH_2)_4$ | —$OCH_2$— | |
| 709 | $C_6H_5$—$(CH_2)_5$ | —$OCH_2$— | |
| 710 | $C_6H_5$—$(CH_2)_6$ | —$OCH_2$— | |
| 711 | 4-t-$C_4H_9$—$C_6H_4$—$CH_2CH(CH_3)CH_2$ | —$OCH_2$— | |
| 712 | H | —CO—$OCH_2$— | |
| 713 | $CH_3$ | —CO—$OCH_2$— | |
| 714 | $C_2H_5$ | —CO—$OCH_2$— | |
| 715 | n-$C_3H_7$ | —CO—$OCH_2$— | |
| 716 | iso-$C_3H_7$ | —CO—$OCH_2$— | |
| 717 | n-$C_4H_9$ | —CO—$OCH_2$— | |
| 718 | $(CH_3)_2CHCH_2$ | —CO—$OCH_2$— | |
| 719 | $CH_3CH_2CH(CH_3)$ | —CO—$OCH_2$— | |
| 720 | tert.$C_4H_9$ | —CO—$OCH_2$— | oil; IR (film): 1727,1480, 1281,1150,771 cm$^{-1}$ |
| 721 | $CH_3CH_2C(CH_3)_2$ | —CO—$OCH_2$— | |
| 722 | $(CH_3)_3CCH_2$ | —CO—$OCH_2$— | |
| 723 | $(CH_3)_2CHCH_2CH_2$ | —CO—$OCH_2$— | |
| 724 | $CH_3CH_2CH_2CH(C_2H_5)$ | —CO—$OCH_2$— | |
| 725 | n-$C_5H_{11}$ | —CO—$OCH_2$— | |
| 726 | n-$C_6H_{13}$ | —CO—$OCH_2$— | |
| 727 | n-$C_7H_{15}$ | —CO—$OCH_2$— | |
| 728 | n-$C_8H_{17}$ | —CO—$OCH_2$— | |
| 729 | n-$C_9H_{19}$ | —CO—$OCH_2$— | |
| 730 | n-$C_{10}H_{21}$ | —CO—$OCH_2$— | |
| 731 | n-$C_{15}H_{31}$ | —CO—$OCH_2$— | |
| 732 | n-$C_{17}H_{35}$ | —CO—$OCH_2$— | |
| 733 | $CH_2$=CH | —CO—$OCH_2$— | |
| 734 | $CH_2$=$C(CH_3)$ | —CO—$OCH_2$— | |
| 735 | $CH_3CH$=CH | —CO—$OCH_2$— | |
| 736 | $CH_3CH$=$C(CH_3)$ | —CO—$OCH_2$— | |
| 737 | $(CH_3)_2C$=CH | —CO—$OCH_2$— | |
| 738 | $CH_2$=$CHCH_2$ | —CO—$OCH_2$— | |
| 739 | $CH_3CH$=$CHCH_2$ | —CO—$OCH_2$— | |
| 740 | $(CH_3)_2C$=$CHCH_2$ | —CO—$OCH_2$— | |
| 741 | $CH_3CH$=CH—CH=CH | —CO—$OCH_2$— | |
| 742 | $(CH_3)_2C$=$CHCH_2CH_2C(CH_3)$=CH | —CO—$OCH_2$— | |
| 743 | $(CH_3)_2CHCH_2CH_2CH_2(CH_3)CH_2$ | —CO—$OCH_2$— | |
| 744 | $(CH_3)_2C$=$CHCH_2CH_2CH(CH_3)CH_2$ | —CO—$OCH_2$— | |
| 745 | HC≡C | —CO—$OCH_2$— | |
| 746 | $C_6H_5$—C≡C | —CO—$OCH_2$— | |
| 747 | $CH_3OCH_2$ | —CO—$OCH_2$— | |
| 748 | $C_2H_5OCH_2$ | —CO—$OCH_2$— | |
| 749 | $CH_3CH(OCH_3)$ | —CO—$OCH_2$— | |
| 750 | CN—$CH_2$ | —CO—$OCH_2$— | |
| 751 | cyclopropyl | —CO—$OCH_2$— | oil; IR (Film): 2958,1726, 1399,1168,1082,772 cm$^{-1}$ |
| 752 | cyclobutyl | —CO—$OCH_2$— | |
| 753 | cyclopentyl | —CO—$OCH_2$— | |
| 754 | cyclohexyl | —CO—$OCH_2$— | |
| 755 | 1-methylcyclopropyl | —CO—$OCH_2$— | oil; IR (film): 1724,1323,1214,1197, 1157,771,75 cm$^{-1}$ |
| 756 | 2,2-dichloro-1-methyl-cyclopropyl | —CO—$OCH_2$— | |
| 757 | 2,2-dichloro-3,3-dimethyl-cyclopropyl | —CO—$OCH_2$— | |
| 758 | 2,2,3,3-tetramethylcyclopropyl | —CO—$OCH_2$— | |
| 759 | 2-(2'-methyl-1'-propenyl-)-3,3-dimethylcyclopropyl | —CO—$OCH_2$— | |
| 760 | 2-(2',2'-difluorovinyl)-3,3-dimethylcyclopropyl | —CO—$OCH_2$— | |
| 761 | 2-(2',2'-dichlorovinyl)-3,3-dimethylcyclopropyl | —CO—$OCH_2$— | |
| 762 | 2-(2',2'-dibromovinyl)-3,3-dimethylcyclopropyl | —CO—$OCH_2$— | |
| 763 | 2-phenylcyclopropyl | —CO—$OCH_2$— | |
| 764 | 2-(4'-chlorophenyl)cyclopropyl | —CO—$OCH_2$— | |
| 765 | 2,2-dichloro-3-phenylcyclopropyl | —CO—$OCH_2$— | |
| 766 | 2-carbomethoxy-cyclopropyl | —CO—$OCH_2$— | |
| 767 | $Cl_2CH$ | —CO—$OCH_2$— | |
| 768 | $Cl_2CH$ | —CO—$OCH_2$— | |
| 769 | $Cl_3C$ | —CO—$OCH_2$— | |
| 770 | $BrCH_2$ | —CO—$OCH_2$— | |
| 771 | $CF_3$ | —CO—$OCH_2$— | |
| 772 | $CH_3CH(Cl)$ | —CO—$OCH_2$— | |
| 773 | $C_6H_5$ (=phenyl) | —CO—$OCH_2$— | oil; IR (film) |

1722,1451,1314,1270
1213,1110,713 cm$^{-1}$

| | | |
|---|---|---|
| 774 | 2-CH$_3$—C$_6$H$_4$ | —CO—OCH$_2$— |
| 775 | 3-CH$_3$—C$_6$H$_4$ | —CO—OCH$_2$— |
| 776 | 4-CH$_3$—C$_6$H$_4$ | —CO—OCH$_2$— |
| 777 | 2,3-(CH$_3$)$_2$—C$_6$H$_3$ | —CO—OCH$_2$— |
| 778 | 2,4-(CH$_3$)$_2$—C$_6$H$_3$ | —CO—OCH$_2$— |
| 779 | 2,6-(CH$_3$)$_2$—C$_6$H$_3$ | —CO—OCH$_2$— |
| 780 | 3,4-(CH$_3$)$_2$—C$_6$H$_3$ | —CO—OCH$_2$— |
| 781 | 3,5-(CH$_3$)$_2$—C$_6$H$_3$ | —CO—OCH$_2$— |
| 782 | 2,4,6-(CH$_3$)$_2$—C$_6$H$_2$ | —CO—OCH$_2$— |
| 783 | 4-t-C$_4$H$_9$—C$_6$H$_4$ | —CO—OCH$_2$— |
| 784 | 2-C$_6$H$_5$—C$_6$H$_4$ | —CO—OCH$_2$— |
| 785 | 4-C$_6$H$_5$—C$_6$H$_4$ | —CO—OCH$_2$— |
| 786 | 2-Cl—C$_6$H$_4$ | —CO—OCH$_2$— |
| 787 | 3-Cl—C$_6$H$_4$ | —CO—OCH$_2$— |
| 788 | 4-Cl—C$_6$H$_4$ | —CO—OCH$_2$— |
| 789 | 2,4-Cl$_2$—C$_6$H$_3$ | —CO—OCH$_2$— |
| 790 | 2,5-Cl$_2$—C$_6$H$_3$ | —CO—OCH$_2$— |
| 791 | 2,6-Cl$_2$—C$_6$H$_3$ | —CO—OCH$_2$— |
| 792 | 3,4-Cl$_2$—C$_6$H$_3$ | —CO—OCH$_2$— |
| 793 | 3,5-Cl$_2$—C$_6$H$_3$ | —CO—OCH$_2$— |
| 794 | 2,4,5-Cl$_3$—C$_6$H$_3$ | —CO—OCH$_2$— |
| 795 | 2,3,4,5,6-Cl$_5$—C$_6$ | —CO—OCH$_2$— |
| 796 | 6-F,2-Cl—C$_6$H$_3$ | —CO—OCH$_2$— |
| 797 | 2-F—C$_6$H$_4$ | —CO—OCH$_2$— |
| 798 | 3-F—C$_6$H$_4$ | —CO—OCH$_2$— |
| 799 | 4-F—C$_6$H$_4$ | —CO—OCH$_2$— |
| 800 | 2,4-F$_2$—C$_6$H$_3$ | —CO—OCH$_2$— |
| 801 | 2,6-F$_2$—C$_6$H$_3$ | —CO—OCH$_2$— |
| 802 | 2,3,4,5,6-F$_5$—C$_6$ | —CO—OCH$_2$— |
| 803 | 2-Br—C$_6$H$_4$ | —CO—OCH$_2$— |
| 804 | 3-Br—C$_6$H$_4$ | —CO—OCH$_2$— |
| 805 | 4-Br—C$_6$H$_4$ | —CO—OCH$_2$— |
| 806 | 2-CF$_3$—C$_6$H$_4$ | —CO—OCH$_2$— |
| 807 | 3-CF$_3$—C$_6$H$_4$ | —CO—OCH$_2$— |
| 808 | 4-CF$_3$—C$_6$H$_4$ | —CO—OCH$_2$— |
| 809 | 2-OCH$_3$—C$_6$H$_4$ | —CO—OCH$_2$— |
| 810 | 3-OCH$_3$—C$_6$H$_4$ | —CO—OCH$_2$— |
| 811 | 4-OCH$_3$—C$_6$H$_4$ | —CO—OCH$_2$— |
| 812 | 3,4-(OCH$_3$)$_2$—C$_6$H$_3$ | —CO—OCH$_2$— |
| 813 | 3,4,5-(OCH$_3$)$_3$—C$_6$H$_3$ | —CO—OCH$_2$— |
| 814 | 4-t-C$_4$H$_9$O—C$_6$H$_4$ | —CO—OCH$_2$— |
| 815 | 2-phenoxy-C$_6$H$_4$ | —CO—OCH$_2$— |
| 816 | 3-phenoxy-C$_6$H$_4$ | —CO—OCH$_2$— |
| 817 | 4-phenoxy-C$_6$H$_4$ | —CO—OCH$_2$— |
| 818 | C$_6$H$_5$—CH$_2$ | —CO—OCH$_2$— |
| 819 | 2-F—C$_6$H$_4$—CH$_2$ | —CO—OCH$_2$— |
| 820 | 3-F—C$_6$H$_4$—CH$_2$ | —CO—OCH$_2$— |
| 821 | 4-F—C$_6$H$_4$—CH$_2$ | —CO—OCH$_2$— |
| 822 | 2-Cl—C$_6$H$_4$—CH$_2$ | —CO—OCH$_2$— |
| 823 | 3-Cl—C$_6$H$_4$—CH$_2$ | —CO—OCH$_2$— |
| 824 | 4-Cl—C$_6$H$_4$—CH$_2$ | —CO—OCH$_2$— |
| 825 | 2-Cl,6F—C$_6$H$_3$—CH$_2$ | —CO—OCH$_2$— |
| 826 | 2,4-Cl$_2$—C$_6$H$_3$—CH$_2$ | —CO—OCH$_2$— |
| 827 | 2,6-Cl$_2$—C$_6$H$_3$—CH$_2$ | —CO—OCH$_2$— |
| 828 | 3,5-Cl$_2$—C$_6$H$_3$—CH$_2$ | —CO—OCH$_2$— |
| 829 | 2,4,6-Cl$_3$—C$_6$H$_2$—CH$_2$ | —CO—OCH$_2$— |
| 830 | 2-CH$_3$—C$_6$H$_4$—CH$_2$ | —CO—OCH$_2$— |
| 831 | 3-CH$_3$—C$_6$H$_4$—CH$_2$ | —CO—OCH$_2$— |
| 832 | 4-CH$_3$—C$_6$H$_4$—CH$_2$ | —CO—OCH$_2$— |
| 833 | 4-t-C$_4$H$_9$—C$_6$H$_4$—CH$_2$ | —CO—OCH$_2$— |
| 834 | 2,4-(CH$_3$)$_2$—C$_6$H$_3$—CH$_2$ | —CO—OCH$_2$— |
| 835 | 2,6-(CH$_3$)$_2$—C$_6$H$_3$—CH$_2$ | —CO—OCH$_2$— |
| 836 | 2,4,6-(CH$_3$)$_3$—C$_6$H$_2$—CH$_2$ | —CO—OCH$_2$— |
| 837 | 2-OCH$_3$—C$_6$H$_4$—CH$_2$ | —CO—OCH$_2$— |
| 838 | 3-OCH$_3$—C$_6$H$_4$—CH$_2$ | —CO—OCH$_2$— |
| 839 | 4-OCH$_3$—C$_6$H$_4$—CH$_2$ | —CO—OCH$_2$— |
| 840 | 2-CF$_3$—C$_6$H$_4$—CH$_2$ | —CO—OCH$_2$— |
| 841 | 3-CF$_3$—C$_6$H$_4$—CH$_2$ | —CO—OCH$_2$— |
| 842 | 4-CF$_3$—C$_6$H$_4$—CH$_2$ | —CO—OCH$_2$— |
| 843 | 4-O-t-C$_4$H$_9$—C$_6$H$_4$—CH$_2$ | —CO—OCH$_2$— |
| 844 | 4-O—C$_6$H$_5$—C$_6$H$_4$—CH$_2$ | —CO—OCH$_2$— |
| 845 | 4-C$_6$H$_5$—C$_6$H$_4$—CH$_2$ | —CO—OCH$_2$— |
| 846 | 2-Br—C$_6$H$_4$—CH$_2$ | —CO—OCH$_2$— |
| 847 | 3-Br—C$_6$H$_4$—CH$_2$ | —CO—OCH$_2$— |
| 848 | 4-Br—C$_6$H$_4$—CH$_2$ | —CO—OCH$_2$— |
| 849 | C$_6$H$_5$—CH(CH$_3$) | —CO—OCH$_2$— |
| 850 | C$_6$H$_5$—CH(C$_2$H$_5$) | —CO—OCH$_2$— |
| 851 | C$_6$H$_5$—CH(iso-C$_3$H$_7$) | —CO—OCH$_2$— |
| 852 | C$_6$H$_5$—CH(OH) | —CO—OCH$_2$— |
| 853 | 2-OCH$_3$—C$_6$H$_4$—CH(OH) | —CO—OCH$_2$— |

-continued

| | | | |
|---|---|---|---|
| 854 | 4-OCH₃—C₆H₄—CH(OH) | —CO—OCH₂— | |
| 855 | 3,4-(OCH₃)₂—C₆H₃—CH(OH) | —CO—OCH₂— | |
| 856 | 2-OCH₃—C₆H₄—CH(OCH₃) | —CO—OCH₂— | |
| 857 | 4-OCH₃—C₆H₄—CH(OCH₃) | —CO—OCH₂— | |
| 858 | 3,4-(OCH₃)₂—C₆H₃—CH(OCH₃) | —CO—OCH₂— | |
| 859 | C₆H₅—CH₂CH₂ | —CO—OCH₂— | |
| 860 | C₆H₅—CH₂CH(CH₃) | —CO—OCH₂— | |
| 861 | 4-t-C₄H₉—C₆H₄—CH₂CH₂ | —CO—OCH₂— | |
| 862 | 4-t-C₄H₉—C₆H₄—CH₂CH(CH₃) | —CO—OCH₂— | |
| 863 | 2-Cl—C₆H₄—CH₂CH₂ | —CO—OCH₂— | |
| 864 | 3-Cl—C₆H₄—CH₂CH₂ | —CO—OCH₂— | |
| 865 | 4-Cl—C₆H₄—CH₂CH₃ | —CO—OCH₂— | |
| 866 | C₆H₅—CH=CH | —CO—OCH₂— | oil; IR (film) 1719,1637,1311,1204 1164,768 cm⁻¹ |
| 867 | 2-Cl—C₆H₄—CH=CH | —CO—OCH₂— | |
| 868 | 3-Cl—C₆H₄—CH=CH | —CO—OCH₂— | |
| 869 | 4-Cl—C₆H₄—CH=CH | —CO—OCH₂— | |
| 870 | 2,4-Cl₂—C₆H₃—CH=CH | —CO—OCH₂— | |
| 871 | 2-F—C₆H₄—CH=CH | —CO—OCH₂— | |
| 872 | 4-F—C₆H₄—CH=CH | —CO—OCH₂— | |
| 873 | 2-CH₃—C₆H₄—CH=CH | —CO—OCH₂— | |
| 874 | 4-CH₃—C₆H₄—CH=CH | —CO—OCH₂— | |
| 875 | 4-t-C₄H₉—C₆H₄—CH=CH | —CO—OCH₂— | |
| 876 | 2-OCH₃—C₆H₄—CH=CH | —CO—OCH₂— | |
| 877 | 4-OCH₃—C₆H₄—CH=CH | —CO—OCH₂— | |
| 878 | 4-Phenoxy-C₆H₄—CH=CH | —CO—OCH₂— | |
| 879 | C₆H₅—(CH₂)₃ | —CO—OCH₂— | |
| 880 | C₆H₅—CH₂CH(CH₃)CH₂ | —CO—OCH₂— | |
| 881 | C₆H₅—(CH₂)₄ | —CO—OCH₂— | |
| 882 | C₆H₅—(CH₂)₅ | —CO—OCH₂— | |
| 883 | C₆H₅—(CH₂)₆ | —CO—OCH₂— | |
| 884 | 4-t-C₄H₉—C₆H₄—CH₂CH(CH₃)CH₂ | —CO—OCH₂— | |
| 885 | C₆H₅ | —C≡C— | |
| 886 | 2-Cl—C₆H₄ | —C≡C— | |
| 887 | 3-Cl—C₆H₄ | —C≡C— | |
| 888 | 4-Cl—C₆H₄ | —C≡C— | |
| 889 | C₆H₅OCH₂ | —C≡C— | |
| 890 | 2-Cl—C₆H₅OCH₂ | —C≡C— | |
| 891 | 3-Cl—C₆H₅OCH₂ | —C≡C— | |
| 892 | 4-Cl—C₆H₅OCH₂ | —C≡C— | |
| 893 | CH₃OOC | —C≡C— | |
| 894 | t-C₄H₉OOC | —C≡C— | |
| 895 | C₆H₆ | —CH₂— | |
| 896 | 2-F—C₆H₄ | —CH₂— | |
| 897 | 3-F—C₆H₄ | —CH₂— | |
| 898 | 4-F—C₆H₄ | —CH₂— | |
| 899 | 2-Cl—C₆H₄ | —CH₂— | |
| 900 | 3-Cl—C₆H₄ | —CH₂— | |
| 901 | 4-Cl—C₆H₄ | —CH₂— | |
| 902 | 2Cl,6F—C₆H₃ | —CH₂— | |
| 903 | 2,4-Cl₂—C₆H₃ | —CH₂— | |
| 904 | 2,6-Cl₂—C₆H₃ | —CH₂— | |
| 905 | 3,5-Cl₂—C₆H₃ | —CH₂— | |
| 906 | 2,4,6-Cl₃—C₆H₂ | —CH₂— | |
| 907 | 2-CH₃—C₆H₄ | —CH₂— | |
| 908 | 3-CH₃—C₆H₄ | —CH₂— | |
| 909 | 4-CH₃—C₆H₄ | —CH₂— | |
| 910 | 4-t-C₄H₉—C₆H₄ | —CH₂— | |
| 911 | 2,4-(CH₃)₂—C₆H₃ | —CH₂— | |
| 912 | 2,6-(CH₃)₂—C₆H₃ | —CH₂— | |
| 913 | 2,4,6-(CH₃)₃—C₆H₂ | —CH₂— | |
| 914 | 2-OCH₃—C₆H₄ | —CH₂— | |
| 915 | 3-OCH₃—C₆H₄ | —CH₂— | |
| 916 | 4-OCH₃—C₆H₄ | —CH₂— | |
| 917 | 2-CF₃—C₆H₄ | —CH₂— | |
| 918 | 3-CF₃—C₆H₄ | —CH₂— | |
| 919 | 4-CF₃—C₆H₄ | —CH₂— | |
| 920 | 4-O-t-C₄H₉—C₆H₄ | —CH₂— | |
| 921 | 4-O—C₆H₅—C₆H₄ | —CH₂— | |
| 922 | 4-C₆H₅—C₆H₄ | —CH₂— | |
| 923 | 2-Br—C₆H₄ | —CH₂— | |
| 924 | 4-Br—C₆H₄ | —CH₂— | |
| 925 | Br | —CH₂— | |
| 926 | Br⁻(C₆H₅)₃P⁺ | —CH₂— | ⎫ v. specification for data |
| 927 | Cl⁻(C₆H₅)₃P⁺ | —CH₂— | ⎭ |
| 928 | Br₂ | \CH—/ | |

-continued

| | | |
|---|---|---|
| 929 | Cl₂ |  |
| 930 | O=CH | — |
| 931 | iso-C₃H₇ | O |
| 932 | CH₃CH₂CH(CH₃) | O |
| 933 | ter.C₄H₉ | O |
| 934 | CH₃CH₂C(CH₃)₂ | O |
| 935 | CH₃CH₂CH₂CH(C₂H₅) | O |
| 936 | CH₂=CH—CH₂ | O |
| 937 | CH₃CH=CH—CH₂ | O |
| 938 | (CH₃)₂C=CH—CH₂ | O |
| 939 | CH₃OCH₂ | O |
| 940 | CNCH₂ | O |
| 941 | cyclopropyl | O |
| 942 | cyclobutyl | O |
| 943 | cyclopentyl | O |
| 944 | cyclohexyl | O |
| 945 | 1-methylcyclohexyl | O |
| 946 | 1-methylcyclopropyl | O |
| 947 | Cl₃C | O |
| 948 | CF₃C | O |
| 949 | C₆H₅ (=phenyl) | O |
| 950 | 2-CH₃—C₆H₄ | O |
| 951 | 3-CH₃—C₆H₄ | O |
| 952 | 4-CH₃—C₆H₄ | O |
| 953 | 2,3-(CH₃)₂—C₆H₃ | O |
| 954 | 2,4-(CH₃)₂—C₆H₃ | O |
| 955 | 2,6-(CH₃)₂—C₆H₃ | O |
| 956 | 3,4-(CH₃)₂—C₆H₃ | O |
| 957 | 3,5-(CH₃)₂—C₆H₃ | O |
| 958 | 2,4,6-(CH₃)₂—C₆H₂ | O |
| 959 | 4-t-C₄H₉—C₆H₄ | O |
| 960 | 2-C₆H₅—C₆H₄ | O |
| 961 | 4-C₆H₅—C₆H₄ | O |
| 962 | 2-Cl—C₆H₄ | O |
| 963 | 3-Cl—C₆H₄ | O |
| 964 | 4-Cl—C₆H₄ | O |
| 965 | 2,4-Cl₂—C₆H₃ | O |
| 966 | 2,5-Cl₂—C₆H₃ | O |
| 967 | 2,6-Cl₂—C₆H₃ | O |
| 968 | 3,4-Cl₂—C₆H₃ | O |
| 969 | 3,5-Cl₂—C₆H₃ | O |
| 970 | 2,4,5-Cl₃—C₆H₂ | O |
| 971 | 2,3,4,5,6-Cl₅—C₆ | O |
| 972 | 6-F,2-Cl—C₆H₃ | O |
| 973 | 2-F—C₆H₄ | O |
| 974 | 3-F—C₆H₄ | O |
| 975 | 4-F—C₆H₄ | O |
| 976 | 2,4-F₂—C₆H₃ | O |
| 977 | 2,6-F₂—C₆H₃ | O |
| 978 | 2,3,4,5,6-F₅—C₆ | O |
| 979 | 2-Br—C₆H₄ | O |
| 980 | 3-Br—C₆H₄ | O |
| 981 | 4-Br—C₆H₄ | O |
| 982 | 2-CF₃—C₆H₄ | O |
| 983 | 3-CF₃—C₆H₄ | O |
| 984 | 4-CF₃—C₆H₄ | O |
| 985 | 2-OCH₃—C₆H₄ | O |
| 986 | 3-OCH₃—C₆H₄ | O |
| 987 | 4-OCH₃—C₆H₄ | O |
| 988 | 3,4-(OCH₃)₂—C₆H₃ | O |
| 989 | 3,4,5-(OCH₃)₃—C₆H₂ | O |
| 990 | 4-t-C₄H₉O—C₆H₄ | O |
| 991 | 2-phenoxy-C₆H₄ | O |
| 992 | 3-phenoxy-C₆H₄ | O |
| 993 | 4-phenoxy-C₆H₄ | O |
| 994 | C₆H₅ | —SCH₂— |
| 995 | 2-F—C₆H₄ | —SCH₂— |
| 996 | 3-F—C₆H₄ | —SCH₂— |
| 997 | 4-F—C₆H₄ | —SCH₂— |
| 998 | 2-Cl—C₆H₄ | —SCH₂— |
| 999 | 3-Cl—C₆H₄ | —SCH₂— |
| 1000 | 4-Cl—C₆H₄ | —SCH₂— |
| 1001 | 2Cl,6F—C₆H₃ | —SCH₂— |
| 1002 | 2,4-Cl₂—C₆H₃ | —SCH₂— |
| 1003 | 2,6-Cl₂—C₆H₃ | —SCH₂— |
| 1004 | 3,5-Cl₂—C₆H₃ | —SCH₂— |
| 1005 | 2,4,6-Cl₃—C₆H₂ | —SCH₂— |

-continued

| | | |
|---|---|---|
| 1006 | 2-CH$_3$—C$_6$H$_4$ | —SCH$_2$— |
| 1007 | 3-CH$_3$—C$_6$H$_4$ | —SCH$_2$— |
| 1008 | 4-CH$_3$—C$_6$H$_4$ | —SCH$_2$— |
| 1009 | 4-t-C$_4$H$_9$—C$_6$H$_4$ | —SCH$_2$— |
| 1010 | 2,4-(CH$_3$)$_2$—C$_6$H$_3$ | —SCH$_2$— |
| 1011 | 2,6-(CH$_3$)$_2$—C$_6$H$_3$ | —SCH$_2$— |
| 1012 | 2,4,6-(CH$_3$)$_3$—C$_6$H$_2$ | —SCH$_2$— |
| 1013 | 2-OCH$_3$—C$_6$H$_4$ | —SCH$_2$— |
| 1014 | 3-OCH$_3$—C$_6$H$_4$ | —SCH$_2$— |
| 1015 | 4-OCH$_3$—C$_6$H$_4$ | —SCH$_2$— |
| 1016 | 2-CF$_3$—C$_6$H$_4$ | —SCH$_2$— |
| 1017 | 3-CF$_3$—C$_6$H$_4$ | —SCH$_2$— |
| 1018 | 4-CF$_3$—C$_6$H$_4$ | —SCH$_3$ |
| 1019 | 4-O-t-C$_4$H$_9$—C$_6$H$_4$ | —SCH$_2$— |
| 1020 | 4-O-C$_6$H$_5$—C$_6$H$_4$ | —SCH$_2$— |
| 1021 | 4-C$_6$H$_5$—C$_6$H$_4$ | —SCH$_2$— |
| 1022 | 2-Br—C$_6$H$_4$ | —SCH$_2$— |
| 1023 | 4-Br—C$_6$H$_4$ | —SCH$_2$— |
| 1024 | C$_6$H$_5$ | —S— |
| 1025 | 2-Cl—C$_6$H$_4$ | —S— |
| 1026 | 3-Cl—C$_6$H$_4$ | —S— |
| 1027 | 4-Cl—C$_6$H$_4$ | —S— |
| 1028 | 2-CH$_3$—C$_6$H$_4$ | —S— |
| 1029 | 4-CH$_3$—C$_6$H$_4$ | —S— |
| 1030 | 4-C$_6$H$_5$—C$_6$H$_5$ | —S— |
| 1031 | CH$_3$ | —S— |
| 1032 | C$_6$H$_5$O | —CH$_2$CH$_2$O— |
| 1033 | 2-Cl—C$_6$H$_4$O | —CH$_2$CH$_2$O— |
| 1034 | 3-Cl—C$_6$H$_4$O | —CH$_2$CH$_2$O— |
| 1035 | 4-Cl—C$_6$H$_4$O | —CH$_2$CH$_2$O— |
| 1036 | 2-CH$_3$—C$_6$H$_4$O | —CH$_2$CH$_2$O— |
| 1037 | 4-CH$_3$—C$_6$H$_4$O | —CH$_2$CH$_2$O— |
| 1038 | 2-OCH$_3$—C$_6$H$_4$O | —CH$_2$CH$_2$O— |
| 1039 | 4-OCH$_3$—C$_6$H$_4$O | —CH$_2$CH$_2$O— |
| 1040 | 2-CF$_3$—C$_6$H$_4$O | —CH$_2$CH$_2$O— |
| 1041 | 4-CF$_3$—C$_6$H$_4$O | —CH$_2$CH$_2$O— |
| 1042 | C$_6$H$_5$OCH$_2$ | —CH$_2$CH$_2$O— |
| 1043 | 2-Cl—C$_6$H$_4$OCH$_2$ | —CH$_2$CH$_2$O— |
| 1044 | 4-Cl—C$_6$H$_4$OCH$_2$ | —CH$_2$CH$_2$O— |
| 1045 | 2-CH$_3$—C$_6$H$_4$OCH$_2$ | —CH$_2$CH$_2$O— |
| 1046 | 4-CH$_3$—C$_6$H$_4$OCH$_2$ | —CH$_2$CH$_2$O— |
| 1047 | 2-OCH$_3$—C$_6$H$_4$OCH$_2$ | —CH$_2$CH$_2$O— |
| 1048 | 4-OCH$_3$—C$_6$H$_4$OCH$_2$ | —CH$_2$CH$_2$O— |
| 1049 | 4-t-C$_4$H$_9$—C$_6$H$_4$OCH$_2$ | —CH$_2$CH$_2$O— |
| 1050 | C$_6$H$_5$OCH$_2$CH$_2$ | —CH$_2$CH$_2$O— |
| 1051 | 2-Cl—C$_6$H$_4$OCH$_2$CH$_2$ | —CH$_2$CH$_2$O— |
| 1052 | 4-Cl—C$_6$H$_4$OCH$_2$CH$_2$ | —CH$_2$CH$_2$O— |
| 1053 | 4-F—C$_6$H$_4$OCH$_2$CH$_2$ | —CH$_2$CH$_2$O— |
| 1054 | 2-CH$_2$—C$_6$H$_4$OCH$_2$CH$_2$ | —CH$_2$CH$_2$O— |
| 1055 | 4-CH$_3$—C$_6$H$_4$OCH$_2$CH$_2$ | —CH$_2$CH$_2$O— |
| 1056 | 2-OCH$_3$—C$_6$H$_4$OCH$_2$CH$_2$ | —CH$_2$CH$_2$O— |
| 1057 | 4-OCH$_3$—C$_6$H$_4$OCH$_2$CH$_2$ | —CH$_2$CH$_2$O— |
| 1058 | 4-t-C$_4$H$_9$—C$_6$H$_4$—OCH$_2$CH$_2$ | CH$_2$CH$_2$O— |
| 1059 | C$_6$H$_5$O(CH$_2$)$_3$ | —CH$_2$CH$_2$O— |
| 1060 | 2-Cl—C$_6$H$_4$O(CH$_2$)$_3$ | —CH$_2$CH$_2$O— |
| 1061 | 4-Cl—C$_6$H$_4$O(CH$_2$)$_3$ | —CH$_2$CH$_2$O— |
| 1062 | C$_6$H$_5$O(CH$_2$)$_4$ | —CH$_2$CH$_2$O— |
| 1063 | 2-Cl—C$_6$H$_4$—O(CH$_2$)$_4$ | —CH$_2$CH$_2$O— |
| 1064 | 4-Cl—C$_6$H$_4$O(CH$_2$)$_4$ | —CH$_2$CH$_2$O— |
| 1065 | C$_6$H$_5$O(CH$_2$)$_5$ | —CH$_2$CH$_2$O— |
| 1066 | 2-Cl—C$_6$H$_4$O(CH$_2$)$_5$ | —CH$_2$CH$_2$O— |
| 1067 | 4-Cl—C$_6$H$_4$O(CH$_2$)$_5$ | —CH$_2$CH$_2$O— |
| 1068 | C$_6$H$_5$O(CH$_2$)$_6$ | —CH$_2$CH$_2$O— |
| 1069 | C$_6$H$_5$OCH$_2$CH$_2$O | —CH$_2$CH$_2$O— |
| 1070 | C$_6$H$_5$ | —CO—O— |
| 1071 | 2-Cl—C$_6$H$_4$ | —CO—O— |
| 1072 | 3-Cl—C$_6$H$_4$ | —CO—O— |
| 1073 | 4-Cl—C$_6$H$_4$ | —CO—O— |
| 1074 | 2-CH$_3$—C$_6$H$_4$ | —CO—O— |
| 1075 | 4-CH$_3$—C$_6$H$_4$ | —CO—O— |
| 1076 | 4-C$_6$H$_5$—C$_6$H$_4$ | —CO—O— |
| 1077 | C$_6$H$_5$ | —CO—O— |
| 1078 | 2-Cl—C$_6$H$_4$ | —CO—O— |
| 1079 | 3-Cl—C$_6$H$_4$ | —CO—O— |
| 1080 | 4-Cl—C$_6$H$_4$ | —CO—O— |
| 1081 | 2-CH$_3$—C$_6$H$_4$ | —CO—O— |
| 1082 | CH$_3$ | —CO—O— |
| 1083 | t-C$_4$H$_9$ | —CO—O— |
| 1084 | CH$_2$C$_6$H$_5$ | —CO—O— |
| 1085 | C$_6$H$_5$ | —HN—CO—O— |
| 1086 | 2-Cl—C$_6$H$_4$ | —HN—CO—O— |
| 1087 | 4-Cl—C$_6$H$_4$ | —HN—CO—O— |

-continued

| | | |
|---|---|---|
| 1088 | C₆H₁₁ | —HN—CO—O— |
| 1089 | n-C₄H₉ | —HN—CO—O— |
| 1090 | 2-furyl | —CH=CH— |
| 1091 | 5-nitro-2-furyl | —CH=CH— |
| 1092 | 5-chloro-2-furyl | —CH=CH— |
| 1093 | 2-(2'-furyl)-ethenyl | —CH=CH— |
| 1094 | 2-(5'-nitro-2'-furyl)ethenyl | —CH=CH— |
| 1095 | 3-furyl | —CH=CH— |
| 1096 | 5-nitro-3-furyl | —CH=CH— |
| 1097 | 5-chloro-3-furyl | —CH=CH— |
| 1098 | 2-(3'-furyl)ethenyl | —CH=CH— |
| 1099 | 2-(5'-nitro-3'-furyl)ethenyl | —CH=CH— |
| 1100 | benzofuran-2-yl | —CH=CH— |
| 1101 | benzofuran-3-yl | —CH=CH— |
| 1102 | 2-thienyl | —CH=CH— |
| 1103 | 5-nitro-2-thienyl | —CH=CH— |
| 1104 | 5-chloro-2-thienyl | —CH=CH— |
| 1105 | 2-(2'-thienyl)ethenyl | —CH=CH— |
| 1106 | 2-(5'-nitro-2'-thienyl)ethenyl | —CH=CH— |
| 1107 | 3-thienyl | —CH=CH— |
| 1108 | 5-nitro-3-thienyl | —CH=CH— |
| 1109 | 5-chloro-3-thienyl | —CH=CH— |
| 1110 | 2-(3'-thienyl)ethenyl | —CH=CH— |
| 1111 | 2-(5'-nitro-3'-thienyl)ethenyl | —CH=CH— |
| 1112 | benzothien-2-yl | —CH=CH— |
| 1113 | benzothien-3-yl | —CH=CH— |
| 1114 | N-methyl-pyrrol-2-yl | —CH=CH— |
| 1115 | N-methyl-pyrrol-3-yl | —CH=CH— |
| 1116 | N-methyl-pyrazol-3-yl | —CH=CH— |
| 1117 | N-methyl-pyrazol-4-yl | —CH=CH— |
| 1118 | N-methyl-pyrazol-5-yl | —CH=CH— |
| 1119 | N-methyl-imidazol-2-yl | —CH=CH— |
| 1120 | N-methyl-imidazol-4-yl | —CH=CH— |
| 1121 | N-methyl-imidazol-5-yl | —CH=CH— |
| 1122 | 1-methyl-1,2,3-triazol-4-yl | —CH=CH— |
| 1123 | 1-methyl-1,2,3-triazol-5-yl | —CH=CH— |
| 1124 | 1-methyl-1,2,4-triazol-3-yl | —CH=CH— |
| 1125 | 1-methyl-1,2,4-triazol-5-yl | —CH=CH— |
| 1126 | 1-methyl-tetrazol-5-yl | —CH=CH— |
| 1127 | isoxazol-3-yl | —CH=CH— |
| 1128 | isoxazol-4-yl | —CH=CH— |
| 1129 | isoxazol-5-yl | —CH=CH— |
| 1130 | benisoxazol-3-yl | —CH=CH— |
| 1131 | benzoxazol-2-yl | —CH=CH— |
| 1132 | oxazol-2-yl | —CH=CH— |
| 1133 | oxazol-4-yl | —CH=CH— |
| 1134 | oxazol-5-yl | —CH=CH— |
| 1135 | thiazol-2-yl | —CH=CH— |
| 1136 | thiazol-4-yl | —CH=CH— |
| 1137 | thiazol-5-yl | —CH=CH— |
| 1138 | benzthiazol-2-yl | —CH=CH— |
| 1139 | benzisothiazol-3-yl | —CH=CH— |
| 1140 | isothiazol-3-yl | —CH=CH— |
| 1141 | isothiazol-4-yl | —CH=CH— |
| 1142 | isothiazol-5-yl | —CH=CH— |
| 1143 | 1,2,3-thiadiazol-4-yl | —CH=CH— |

| | | |
|---|---|---|
| 1144 | 1,2,4-thiadiazol-5-yl | —CH=CH— |
| 1145 | 1,3,4-thiadiazol-3-yl | —CH=CH— |
| 1146 | 2-furyl | —CH₂CH₂— |
| 1147 | 5-nitro-2-furyl | —CH₂CH₂— |
| 1148 | 5-chloro-2-furyl | —CH₂CH₂— |
| 1149 | 2-(2'-furyl)-ethenyl | —CH₂CH₂— |
| 1150 | 2-(5'-nitro-2'-furyl)ethenyl | —CH₂CH₂— |
| 1151 | 3-furyl | —CH₂CH₂— |
| 1152 | 5-nitro-3-furyl | —CH₂CH₂— |
| 1153 | 5-chloro-3-furyl | —CH₂CH₂— |
| 1154 | 2-(3'-furyl)ethenyl | —CH₂CH₂— |
| 1155 | 2-(5'-nitro-3'-furyl)ethenyl | —CH₂CH₂— |
| 1156 | benzofuran-2-yl | —CH₂CH₂— |
| 1157 | benzofuran-3-yl | —CH₂CH₂— |
| 1158 | 2-thienyl | —CH₂CH₂— |
| 1159 | 5-nitro-2-thienyl | —CH₂CH₂— |
| 1160 | 5-chloro-2-thienyl | —CH₂CH₂— |
| 1161 | 2-(2'-thienyl)ethenyl | —CH₂CH₂— |
| 1162 | 2-(5'-nitro-2'-thienyl)ethenyl | —CH₂CH₂— |
| 1163 | 3-thienyl | —CH₂CH₂— |
| 1164 | 5-nitro-3-thienyl | —CH₂CH₂— |
| 1165 | 5-chloro-3-thienyl | —CH₂CH₂— |

-continued

| | | |
|---|---|---|
| 1166 | 2-(3'-thienyl)ethenyl | —CH$_2$CH$_2$— |
| 1167 | 2-(5'-nitro-3'-thienyl)ethenyl | —CH$_2$CH$_2$— |
| 1168 | benzothien-2-yl | —CH$_2$CH$_2$— |
| 1169 | benzothien-3-yl | —CH$_2$CH$_2$— |
| 1170 | N-methyl-pyrrol-2-yl | —CH$_2$CH$_2$— |
| 1171 | N-methyl-pyrrol-3-yl | —CH$_2$CH$_2$— |
| 1172 | N-methyl-pyrazol-3-yl | —CH$_2$CH$_2$— |
| 1173 | N-methyl-pyrazol-4-yl | —CH$_2$CH$_2$— |
| 1174 | N-methyl-pyrazol-5-yl | —CH$_2$CH$_2$— |
| 1175 | N-methyl-imidazol-2-yl | —CH$_2$CH$_2$— |
| 1176 | N-methyl-imidazol-4-yl | —CH$_2$CH$_2$— |
| 1177 | N-methyl-imidazol-5-yl | —CH$_2$CH$_2$— |
| 1178 | 1-methyl-1,2,3-triazol-4-yl | —CH$_2$CH$_2$— |
| 1179 | 1-methyl-1,2,3-triazol-5-yl | —CH$_2$CH$_2$— |
| 1180 | 1-methyl-1,2,4-triazol-3-yl | —CH$_2$CH$_2$— |
| 1181 | 1-methyl-1,2,4-triazol-5-yl | —CH$_2$CH$_2$— |
| 1182 | 1-methyl-tetrazol-5-yl | —CH$_2$CH$_2$— |
| 1183 | isoxazol-3-yl | —CH$_2$CH$_2$— |
| 1184 | isoxazol-4-yl | —CH$_2$CH$_2$— |
| 1185 | isoxazol-5-yl | —CH$_2$CH$_2$— |
| 1186 | benzisoxazol-3-yl | —CH$_2$CH$_2$— |
| 1187 | benzoxazol-2-yl | —CH$_2$CH$_2$— |
| 1188 | oxazol-2-yl | —CH$_2$CH$_2$— |
| 1189 | oxazol-4-yl | —CH$_2$CH$_2$— |
| 1190 | oxazol-5-yl | —CH$_2$CH$_2$— |
| 1191 | thiazol-2-yl | —CH$_2$CH$_2$— |
| 1192 | thiazol-4-yl | —CH$_2$CH$_2$— |
| 1193 | thiazol-5-yl | —CH$_2$CH$_2$— |
| 1194 | benzthiazol-2-yl | —CH$_2$CH$_2$— |
| 1195 | benzisothiazol-3-yl | —CH$_2$CH$_2$— |
| 1196 | isothiazol-3-yl | —CH$_2$CH$_2$— |
| 1197 | isothiazol-4-yl | —CH$_2$CH$_2$— |
| 1198 | isothiazol-5-yl | —CH$_2$CH$_2$— |
| 1199 | 1,2,3-thiadiazol-4-yl | —CH$_2$CH$_2$— |
| 1200 | 1,2,4-thiadiazol-5-yl | —CH$_2$CH$_2$— |
| 1201 | 1,3,4-thiadiazol-3-yl | —CH$_2$CH$_2$— |
| 1202 | 2-furyl | —CH$_2$O— |
| 1203 | 5-nitro-2-furyl | —CH$_2$O— |
| 1204 | 5-chloro-2-furyl | —CH$_2$O— |
| 1205 | 2-(2'-furyl)-ethenyl | —CH$_2$O— |
| 1206 | 2-(5'-nitro-2'-furyl)ethenyl | —CH$_2$O— |
| 1207 | 3-furyl | —CH$_2$O— |
| 1208 | 5-nitro-3-furyl | —CH$_2$O— |
| 1209 | 5-chloro-3-furyl | —CH$_2$O— |
| 1210 | 2-(3'-furyl)ethenyl | —CH$_2$O— |
| 1211 | 2-(5'-nitro-3'-furanyl)ethenyl | —CH$_2$O— |
| 1212 | benzofuran-2-yl | —CH$_2$O— |
| 1213 | benzofuran-3-yl | —CH$_2$O— |
| 1214 | 2-thienyl | —CH$_2$O— |
| 1215 | 5-nitro-2-thienyl | —CH$_2$O— |
| 1216 | 5-chloro-2-thienyl | —CH$_2$O— |
| 1217 | 2-(2'-thienyl)ethenyl | —CH$_2$O— |
| 1218 | 2-(5'-nitro-2'-thienyl)ethenyl | —CH$_2$O— |
| 1219 | 3-thienyl | —CH$_2$O— |
| 1220 | 5-nitro-3-thienyl | —CH$_2$O— |
| 1221 | 5-chloro-3-thienyl | —CH$_2$O— |
| 1222 | 2-(3'-thienyl)ethenyl | —CH$_2$O— |
| 1223 | 2-(5'-nitro-3'-thienyl)ethenyl | —CH$_2$O— |
| 1224 | benzothien-2-yl | —CH$_2$O— |
| 1225 | benzothien-3-yl | —CH$_2$O— |
| 1226 | N-methyl-pyrrol-2-yl | —CH$_2$O— |
| 1227 | N-methyl-pyrrol-3-yl | —CH$_2$O— |
| 1228 | N-methyl-pyrazol-3-yl | —CH$_2$O— |
| 1229 | N-methy-pyrazol-4-yl | —CH$_2$O— |
| 1230 | N-methyl-pyrazol-5-yl | —CH$_2$O— |
| 1231 | N-methyl-imidazol-2-yl | —CH$_2$O— |
| 1232 | N-methyl-imidazol-4-yl | —CH$_2$O— |
| 1233 | N-methyl-imidazol-5-yl | —CH$_2$O— |
| 1234 | 1-methyl-1,2,3-triazol-4-yl | —CH$_2$O— |
| 1235 | 1-methyl-1,2,3-triazol-5-yl | —CH$_2$O— |
| 1236 | 1-methyl-1,2,4-triazol-3-yl | —CH$_2$O— |
| 1237 | 1-methyl-1,2,4-triazol-5-yl | —CH$_2$O— |
| 1238 | 1-methyl-tetrazol-5-yl | —CH$_2$O— |
| 1239 | isoxazol-3-yl | —CH$_2$O— |
| 1240 | isoxazol-4-yl | —CH$_2$O— |
| 1241 | isoxazol-5-yl | —CH$_2$O— |
| 1242 | benzisoxazol-3-yl | —CH$_2$O— |
| 1243 | benzoxazol-2-yl | —CH$_2$O— |
| 1244 | oxazol-2-yl | —CH$_2$O— |
| 1245 | oxazol-4-yl | —CH$_2$O— |
| 1246 | oxazol-5-yl | —CH$_2$O— |
| 1247 | thiazol-2-yl | —CH$_2$O— |

|   |   |   |
|---|---|---|
| 1248 | thiazol-4-yl | —CH₂O— |
| 1249 | thiazol-5-yl | —CH₂O— |
| 1250 | benzthiasol-2-yl | —CH₂O— |
| 1251 | benzisothiazol-3-yl | —CH₂O— |
| 1252 | isothiazol-3-yl | —CH₂O— |
| 1253 | isothiazol-4-yl | —CH₂O— |
| 1254 | isothiazol-5-yl | —CH₂O— |
| 1255 | 1,2,3-thiadiazol-4-yl | —CH₂O— |
| 1256 | 1,2,4-thiadiazol-5-yl | —CH₂O— |
| 1257 | 1,3,4-thiadiazol-3-yl | —CH₂O— |
| 1258 | 2-furyl | —O— |
| 1259 | 5-nitro-2-furyl | —O— |
| 1260 | 5-chloro-2-furyl | —O— |
| 1261 | 3-furyl | —O— |
| 1262 | 5-nitro-3-furyl | —O— |
| 1263 | 5-chloro-3-furyl | —O— |
| 1264 | benzofuran-2-yl | —O— |
| 1265 | benzofuran-3-yl | —O— |
| 1266 | 2-thienyl | —O— |
| 1267 | 5-nitro-2-thienyl | —O— |
| 1268 | 5-chloro-2-thienyl | —O— |
| 1269 | 3-thienyl | —O— |
| 1270 | 5-nitro-3-thienyl | —O— |
| 1271 | 5-chloro-3-thienyl | —O— |
| 1272 | benzothien-2-yl | —O— |
| 1273 | benzothien-3-yl | —O— |
| 1274 | N-methyl-pyrrol-2-yl | —O— |
| 1275 | N-methyl-pyrrol-3-yl | —O— |
| 1276 | N-methyl-pyrazol-3-yl | —O— |
| 1277 | N-methyl-pyrazol-4-yl | —O— |
| 1278 | N-methyl-pyrazol-5-yl | —O— |
| 1279 | N-methyl-imidazol-2-yl | —O— |
| 1280 | N-methyl-imidazol-4-yl | —O— |
| 1281 | N-methyl-imidazol-5-yl | —O— |
| 1282 | 1-methyl-1,2,3-triazol-4-yl | —O— |
| 1283 | 1-methyl-1,2,3-triazol-5-yl | —O— |
| 1284 | 1-methyl-1,2,4-triazol-3-yl | —O— |
| 1285 | 1-methyl-1,2,4-triazol-5-yl | —O— |
| 1286 | 1-methyl-tetrazol-5-yl | —O— |
| 1287 | isoxazol-3-yl | —O— |
| 1288 | isoxazol-4-yl | —O— |
| 1289 | isoxazol-5-yl | —O— |
| 1290 | benzisoxazol-3-yl | —O— |
| 1291 | benzoxazol-2-yl | —O— |
| 1292 | oxazol-2-yl | —O— |
| 1293 | oxazol-4-yl | —O— |
| 1294 | oxazol-5-yl | —O— |
| 1295 | thiazol-2-yl | —O— |
| 1296 | thiazol-4-yl | —O— |
| 1297 | thiazol-5-yl | —O— |
| 1298 | benzthiazol-2-yl | —O— |
| 1299 | benzisothiazol-3-yl | —O— |
| 1300 | isothiazol-3-yl | —O— |
| 1301 | isothiazol-4-yl | —O— |
| 1302 | isothiazol-5-yl | —O— |
| 1303 | 1,3-thiazolo[4,5-b]pyridin-2-yl | —O— |
| 1304 | 2-furyl | —S— |
| 1305 | 5-nitro-2-furyl | —S— |
| 1306 | 5-chloro-2-furyl | —S— |
| 1307 | 3-furyl | —S— |
| 1308 | 5-nitro-3-furyl | —S— |
| 1309 | 5-chloro-3-furyl | —S— |
| 1310 | benzofuran-2-yl | —S— |
| 1311 | benzofuran-3-yl | —S— |
| 1312 | 2-thienyl | —S— |
| 1313 | 5-nitro-2-thienyl | —S— |
| 1314 | 5-chloro-2-thienyl | —S— |
| 1315 | 3-thienyl | —S— |
| 1316 | 5-nitro-3-thienyl | —S— |
| 1317 | 5-chloro-3-thienyl | —S— |
| 1318 | benzothien-2-yl | —S— |
| 1319 | benzothien-3-yl | —S— |
| 1320 | N-methyl-pyrrol-2-yl | —S— |
| 1321 | N-methyl-pyrrol-3-yl | —S— |
| 1322 | N-methyl-pyrazol-3-yl | —S— |
| 1323 | N-methyl-pyrazol-4-yl | —S— |
| 1324 | N-methyl-pyrazol-5-yl | —S— |
| 1325 | N-methyl-imidazol-2-yl | —S— |
| 1326 | N-methyl-imidazol-4-yl | —S— |
| 1327 | N-methyl-imidazol-5-yl | —S— |
| 1328 | 1-methyl-1,2,3-triazol-4-yl | —S— |
| 1329 | 1-methyl-1,2,3-triazol-5-yl | —S— |

-continued

| | | |
|---|---|---|
| 1330 | 1-methyl-1,2,4-triazol-3-yl | —S— |
| 1331 | 1-methyl-1,2,4-triazol-5-yl | —S— |
| 1332 | 1-methyl-tetrazol-5-yl | —S— |
| 1333 | isoxazol-3-yl | —S— |
| 1334 | isoxazol-4-yl | —S— |
| 1335 | isoxazol-5-yl | —S— |
| 1336 | benzisoxazol-3-yl | —S— |
| 1337 | benzoxazol-2-yl | —S— |
| 1338 | oxazol-2-yl | —S— |
| 1339 | oxazol-4-yl | —S— |
| 1340 | oxazol-5-yl | —S— |
| 1341 | thiazol-2-yl | —S— |
| 1342 | oxazol-4-yl | —S— |
| 1343 | oxazol-5-yl | —S— |
| 1344 | thiazol-2-yl | —S— |
| 1345 | thiazol-4-yl | —S— |
| 1346 | thiazol-5-yl | —S— |
| 1347 | benzthiazol-2-yl | —S— |
| 1348 | benzisothiazol-3-yl | —S— |
| 1349 | isothiazol-3-yl | —S— |
| 1350 | isothiazol-4-yl | —S— |
| 1351 | isothiazol-5-yl | —S— |
| 1352 | 1,3,-thiazolo[4,5-b]pyridin-2-yl | —S— |
| 1353 | 2-furyl | —OCH$_2$— |
| 1354 | 5-nitro-2-furyl | —OCH$_2$— |
| 1355 | 5-chloro-2-furyl | —OCH$_2$— |
| 1356 | 3-Furyl | —OCH$_2$— |
| 1357 | 5-nitro-3-furyl | —OCH$_2$— |
| 1358 | 5-chloro-3-furyl | —OCH$_2$— |
| 1359 | benzofuran-2-yl | —OCH$_2$— |
| 1360 | benzofuran-3-yl | —OCH$_2$— |
| 1361 | 2-thienyl | —OCH$_2$— |
| 1362 | 5-nitro-2-thienyl | —OCH$_2$— |
| 1363 | 5-chloro-2-thienyl | —OCH$_2$— |
| 1364 | 3-thienyl | —OCH$_2$— |
| 1365 | 5-nitro-3-thienyl | —OCH$_2$— |
| 1366 | 5-chloro-3-thienyl | —OCH$_2$— |
| 1367 | benzothien-2-yl | —OCH$_2$— |
| 1368 | benzothien-3-yl | —OCH$_2$— |
| 1369 | N-methyl-pyrrol-2-yl | —OCH$_2$— |
| 1370 | N-methyl-pyrrol-3-yl | —OCH$_2$— |
| 1371 | N-methyl-pyrazol-3-yl | —OCH$_2$— |
| 1372 | N-methyl-pyrazol-4-yl | —OCH$_2$— |
| 1373 | N-methyl-pyrazol-5-yl | —OCH$_2$— |
| 1374 | N-methyl-imidazol-2-yl | —OCH$_2$— |
| 1375 | N-methyl-imidazol-4-yl | —OCH$_2$— |
| 1376 | N-methyl-imidazol-5-yl | —OCH$_2$— |
| 1377 | 1-methyl-1,2,3-triazol-4-yl | —OCH$_2$— |
| 1378 | 1-methyl-1,2,3-triazol-5-yl | —OCH$_2$— |
| 1379 | 1-methyl-1,2,4-triazol-3-yl | —OCH$_2$— |
| 1380 | 1-methyl-1,2,4-triazol-5-yl | —OCH$_2$— |
| 1381 | 1-methyl-tetrazol-5-yl | —OCH$_2$— |
| 1382 | isoxazol-3-yl | —OCH$_2$— |
| 1383 | isoxazol-4-yl | —OCH$_2$— |
| 1384 | isoxazol-5-yl | —OCH$_2$— |
| 1385 | benzisoxazol-3-yl | —OCH$_2$— |
| 1386 | benzoxazol-2-yl | —OCH$_2$— |
| 1387 | oxazol-2-yl | —OCH$_2$— |
| 1389 | oxazol-4-yl | —OCH$_2$— |
| 1390 | oxazol-5-yl | —OCH$_2$— |
| 1391 | thiazol-2-yl | —OCH$_2$— |
| 1392 | thiazol-4-yl | —OCH$_2$— |
| 1393 | thiazol-5-yl | —OCH$_2$— |
| 1394 | benzthiazol-2-yl | —OCH$_2$— |
| 1395 | benzisothiazol-3-yl | —OCH$_2$— |
| 1396 | isothiazol-3-yl | —OCH$_2$— |
| 1397 | isothiazol-4-yl | —OCH$_2$— |
| 1398 | isothiazol-5-yl | —OCH$_2$— |
| 1399 | 2-furyl | —SCH$_2$— |
| 1400 | 5-nitro-2-furyl | —SCH$_2$— |
| 1401 | 5-chloro-2-furyl | —SCH$_2$— |
| 1402 | 3-furyl | —SCH$_2$— |
| 1403 | 5-nitro-3-furyl | —SCH$_2$— |
| 1404 | 5-chloro-3-furyl | —SCH$_2$— |
| 1405 | benzofuran-2-yl | —SCH$_2$— |
| 1406 | benzofuran-3-yl | —SCH$_2$— |
| 1407 | 2-thienyl | —SCH$_2$— |
| 1408 | 5-nitro-2-thienyl | —SCH$_2$— |
| 1409 | 5-chloro-2-thienyl | —SCH$_2$— |
| 1410 | 3-thienyl | —SCH$_2$— |
| 1411 | 5-nitro-3-thienyl | —SCH$_2$— |
| 1412 | 5-chloro-3-thienyl | —SCH$_2$— |

| | | | |
|---|---|---|---|
| 1413 | benzothien-2-yl | —SCH₂— | |
| 1414 | benzothien-3-yl | —SCH₂— | |
| 1415 | N-methyl-pyrrol-2-yl | —SCH₂— | |
| 1416 | N-methyl-pyrrol-3-yl | —SCH₂— | |
| 1417 | N-methyl-pyrazol-3-yl | —SCH₂— | |
| 1418 | N-methyl-pyrazol-4-yl | —SCH₂— | |
| 1419 | N-methyl-pyrazol-5-yl | —SCH₂— | |
| 1420 | N-methyl-imidazol-2-yl | —SCH₂— | |
| 1421 | N-methyl-imidazol-4-yl | —SCH₂— | |
| 1422 | N-methyl-imidazol-5-yl | —SCH₂— | |
| 1423 | 1-methyl-1,2,3-triazol-4-yl | —SCH₂— | |
| 1424 | 1-methyl-1,2,3-triazol-5-yl | —SCH₂— | |
| 1425 | 1-methyl-1,2,4-triazol-3-yl | —SCH₂— | |
| 1426 | 1-methyl-1,2,4-triazol-5-yl | —SCH₂— | |
| 1427 | 1-methyl-tetrazol-5-yl | —SCH₂— | |
| 1428 | isoxazol-3-yl | —SCH₂— | |
| 1429 | isoxazol-4-yl | —SCH₂— | |
| 1430 | isoxazol-5-yl | —SCH₂— | |
| 1431 | benzisoxazol-3-yl | —SCH₂— | |
| 1432 | benzoxazol-2-yl | —SCH₂— | |
| 1433 | oxazol-2-yl | —SCH₂— | |
| 1434 | oxazol-4-yl | —SCH₂— | |
| 1435 | oxazol-5-yl | —SCH₂— | |
| 1436 | thiazol-2-yl | —SCH₂— | |
| 1437 | thiazol-4-yl | —SCH₂— | |
| 1438 | thiazol-5-yl | —SCH₂— | |
| 1439 | benzthiazol-2-yl | —SCH₂— | oil; ¹H-NMR (CDCl₃): δ = 3.78(3H), 4.58(2H), 5.83(1H), 6.63(1H), 7.1–7.9(8H) |
| 1440 | benzisothiazol-3-yl | —SCH₂— | |
| 1441 | isothiazol-3-yl | —SCH₂— | |
| 1442 | isothiazol-4-yl | —SCH₂— | |
| 1443 | isothiazol-5-yl | —SCH₂— | |
| 1444 | 1,2,3-thiadiazol-4-yl | —SCH₂— | |
| 1445 | 1,2,4-thiadiazol-5-yl | —SCH₂— | |
| 1446 | 1,3,4-thiadiazol-3-yl | —SCH₂— | |
| 1447 | 2-furyl | —CO—OCH₂— | |
| 1448 | 5-nitro-2-furyl | —CO—OCH₂— | |
| 1449 | 5-chloro-2-furyl | —CO—OCH₂— | |
| 1450 | 2-(2'-furyl)-ethenyl | —CO—OCH₂— | |
| 1451 | 2-(5'-nitro-2'furyl)ethenyl | —CO—OCH₂— | |
| 1452 | 3-furyl | —CO—OCH₂— | |
| 1453 | 5-nitro-3-furyl | —CO—OCH₂— | |
| 1454 | 5-chloro-3-furyl | —CO—OCH₂— | |
| 1455 | 2-(3'-furyl)ethenyl | —CO—OCH₂— | |
| 1456 | 2-(5'-nitro-3'-furanyl)ethenyl | —CO—OCH₂— | |
| 1457 | benzofuran-2-yl | —CO—OCH₂— | |
| 1458 | benzofuran-3-yl | —CO—OCH₂— | |
| 1459 | 2-thienyl | —CO—OCH₂— | |
| 1460 | 5-nitro-2-thienyl | —CO—OCH₂— | |
| 1461 | 5-chloro-2-thienyl | —CO—OCH₂— | |
| 1462 | 2-(2'-thienyl)ethenyl | —CO—OCH₂— | |
| 1463 | 2-(5'-nitro-2'-thienyl)ethenyl | —CO—OCH₂— | |
| 1464 | 3-thienyl | —CO—OCH₂— | |
| 1465 | 5-nitro-3-thienyl | —CO—OCH₂— | |
| 1466 | 5-chloro-3-thienyl | —CO—OCH₂— | |
| 1467 | 2-(3'-thienyl)ethenyl | —CO—OCH₂— | |
| 1468 | 2-(5'-nitro-3'-thienyl)ethenyl | —CO—OCH₂— | |
| 1469 | benzothien-2-yl | —CO—OCH₂— | |
| 1470 | benzothien-3-yl | —CO—OCH₂— | |
| 1471 | N-methyl-pyrrol-2-yl | —CO—OCH₂— | |
| 1472 | N-methyl-pyrrol-3-yl | —CO—OCH₂— | |
| 1473 | N-methyl-pyrazol-3-yl | —CO—OCH₂— | |
| 1474 | N-methyl-pyrazol-4-yl | —CO—OCH₂— | |
| 1475 | N-methyl-pyrazol-5-yl | —CO—OCH₂— | |
| 1476 | N-methyl-imidazol-2-yl | —CO—OCH₂— | |
| 1477 | N-methyl-imidazol-4-yl | —CO—OCH₂— | |
| 1478 | N-methyl-imidazol-5-yl | —CO—OCH₂— | |
| 1479 | 1-methyl-1,2,3-triazol-4-yl | —CO—OCH₂— | |
| 1480 | 1-methyl-1,2,3-triazol-5-yl | —CO—OCH₂— | |
| 1481 | 1-methyl-1,2,4-triazol-3-yl | —CO—OCH₂— | |
| 1482 | 1-methyl-1,2,4-triazol-5-yl | —CO—OCH₂— | |
| 1483 | 1-methyl-tetrazol-5-yl | —CO—OCH₂— | |
| 1484 | isoxazol-3-yl | —CO—OCH₂— | |
| 1485 | isoxazol-4-yl | —CO—OCH₂— | |
| 1486 | isoxazol-5-yl | —CO—OCH₂— | |
| 1487 | benzisoxazol-3-yl | —CO—OCH₂— | |
| 1488 | benzoxazol-2-yl | —CO—OCH₂— | |
| 1489 | oxazol-2-yl | —CO—OCH₂— | |
| 1490 | oxazol-4-yl | —CO—OCH₂— | |
| 1491 | oxazol-5-yl | —CO—OCH₂— | |
| 1492 | thiazol-2-yl | —CO—OCH₂— | |

-continued

| | | |
|---|---|---|
| 1493 | thiazol-4-yl | —CO—OCH$_2$— |
| 1494 | thiazol-5-yl | —CO—OCH$_2$— |
| 1495 | benzthiasol-2-yl | —CO—OCH$_2$— |
| 1496 | benzisothiazol-3-yl | —CO—OCH$_2$— |
| 1497 | isothiazol-3-yl | —CO—OCH$_2$— |
| 1498 | isothioazol-4-yl | —CO—OCH$_2$— |
| 1499 | isothiazol-5-yl | —CO—OCH$_2$— |
| 1500 | 1,2,3-thiadiazol-4-yl | —CO—OCH$_2$— |
| 1501 | 1,2,4-thiadiazol-5-yl | —CO—OCH$_2$— |
| 1502 | 1,3,4-thiadiazol-3-yl | —CO—OCH$_2$— |
| 1503 | 2-furyl | —NH—CO—O— |
| 1504 | 5-nitro-2-furyl | —NH—CO—O— |
| 1505 | 5-chloro-2-furyl | —NH—CO—O— |
| 1506 | 3-furyl | —NH—CO—O— |
| 1507 | 5-nitro-3-furyl | —NH—CO—O— |
| 1508 | 5-chloro-3-furyl | —NH—CO—O— |
| 1509 | benzofuran-2-yl | —NH—CO—O— |
| 1510 | benzofuran-3-yl | —NH—CO—O— |
| 1511 | 2-thienyl | —NH—CO—O— |
| 1512 | 5-nitro-2-thienyl | —NH—CO—O— |
| 1513 | 5-chloro-2-thienyl | —NH—CO—O— |
| 1514 | 3-thienyl | —NH—CO—O— |
| 1515 | 5-nitro-3-thienyl | —NH—CO—O— |
| 1516 | 5-chloro-3-thienyl | —NH—CO—O— |
| 1517 | benzothien-2-yl | —NH—CO—O— |
| 1518 | benzothien-3-yl | —NH—CO—O— |
| 1519 | N-methyl-pyrrol-2-yl | —NH—CO—O— |
| 1520 | N-methyl-pyrrol-3-yl | —NH—CO—O— |
| 1521 | N-methyl-pyrazol-3-yl | —NH—CO—O— |
| 1522 | N-methyl-pyrazol-4-yl | —NH—CO—O— |
| 1523 | N-methyl-pyrazol-5-yl | —NH—CO—O— |
| 1524 | N-methyl-imidazol-4-yl | —NH—CO—O— |
| 1526 | N-methyl-imidazol-5-yl | —NH—CO—O— |
| 1527 | 1-methyl-1,2,3-triazol-4-yl | —NH—CO—O— |
| 1528 | 1-methyl-1,2,3-triazol-5-yl | —NH—CO—O— |
| 1529 | 1-methyl-1,2,4-triazol-3-yl | —NH—CO—O— |
| 1530 | 1-methyl-1,2,4-triazol-5-yl | —NH—CO—O— |
| 1531 | 1-methyl-tetrazol-5-yl | —NH—CO—O— |
| 1532 | isoxazol-3-yl | —NH—CO—O— |
| 1533 | isoxazol-4-yl | —NH—CO—O— |
| 1534 | isoxazol-5-yl | —NH—CO—O— |
| 1535 | benzisoxazol-3-yl | —NH—CO—O— |
| 1536 | benzoxazol-2-yl | —NH—CO—O— |
| 1537 | oxazol-2-yl | —NH—CO—O— |
| 1538 | oxazol-4-yl | —NH—CO—O— |
| 1539 | oxazol-5-yl | —NH—CO—O— |
| 1540 | thiazol-2-yl | —NH—CO—O— |
| 1541 | thiazol-4-yl | —NH—CO—O— |
| 1542 | thiazol-5-yl | —NH—CO—O— |
| 1543 | benzthiazol-2-yl | —NH—CO—O— |
| 1544 | benzisothiazol-3-yl | —NH—CO—O— |
| 1545 | isothiazol-3-yl | —NH—CO—O— |
| 1546 | isothiazol-4-yl | —NH—CO—O— |
| 1547 | isothiazol-5-yl | —NH—CO—O— |
| 1548 | 2-furyl | —CO—O— |
| 1549 | 5-nitro-2-furyl | —CO—O— |
| 1550 | 5-chloro-2-furyl | —CO—O— |
| 1551 | 2-(2'-furyl)-ethenyl | —CO—O— |
| 1552 | 2-(5'-nitro-2'-furyl)ethenyl | —CO—O— |
| 1553 | 3-furyl | —CO—O— |
| 1554 | 5-nitro-3-furyl | —CO—O— |
| 1555 | 5-chloro-3-furyl | —CO—O— |
| 1556 | 2-(3'-furyl)ethenyl | —CO—O— |
| 1557 | 2-(5'-nitro-3'-furanyl)ethenyl | —CO—O— |
| 1558 | benzofuran-2-yl | —CO—O— |
| 1559 | benzofuran-3-yl | —CO—O— |
| 1560 | 2-thienyl | —CO—O— |
| 1561 | 5-nitro-2-thienyl | —CO—O— |
| 1562 | 5-chloro-2-thienyl | —CO—O— |
| 1563 | 2-(2'-thienyl)ethenyl | —CO—O— |
| 1564 | 2-(5'-nitro-2'-thienyl)ethenyl | —CO—O— |
| 1565 | 3-thienyl | —CO—O— |
| 1566 | 5-nitro-3-thienyl | —CO—O— |
| 1567 | 5-chloro-3-thienyl | —CO—O— |
| 1568 | 2-(3'-thienyl)ethenyl | —CO—O— |
| 1569 | 2-(5'-nitro-3'-thienyl)ethenyl | —CO—O— |
| 1570 | benzothien-2-yl | —CO—O— |
| 1571 | benzothien-3-yl | —CO—O— |
| 1572 | N-methyl-pyrrol-2-yl | —CO—O— |
| 1573 | N-methyl-pyrrol-3-yl | —CO—O— |
| 1574 | N-methyl-pyrazol-3-yl | —CO—O— |
| 1575 | N-methyl-pyrazol-4-yl | —CO—O— |

-continued

| | | | |
|---|---|---|---|
| 1576 | N-methyl-pyrazol-5-yl | —CO—O— | |
| 1577 | N-methyl-imidazol-2-yl | —CO—O— | |
| 1578 | N-methyl-imidazol-4-yl | —CO—O— | |
| 1579 | N-methyl-imidazol-5-yl | —CO—O— | |
| 1580 | 1-methyl-1,2,3-triazol-4-yl | —CO—O— | |
| 1581 | 1-methyl-1,2,3-triazol-5-yl | —CO—O— | |
| 1582 | 1-methyl-1,2,4-triazol-3-yl | —CO—O— | |
| 1583 | 1-methyl-1,2,4-triazol-5-yl | —CO—O— | |
| 1584 | 1-methyl-tetrazol-5-yl | —CO—O— | |
| 1585 | isoxazol-3-yl | —CO—O— | |
| 1586 | isoxazol-4-yl | —CO—O— | |
| 1587 | isoxazol-5-yl | —CO—O— | |
| 1588 | benzisoxazol-3-yl | —CO—O— | |
| 1589 | benzoxazol-2-yl | —CO—O— | |
| 1590 | oxazol-2-yl | —CO—O— | |
| 1591 | oxazol-4-yl | —CO—O— | |
| 1592 | oxazol-5-yl | —CO—O— | |
| 1593 | thiazol-2-yl | —CO—O— | |
| 1594 | thiazol-4-yl | —CO—O— | |
| 1595 | thiazol-5-yl | —CO—O— | |
| 1596 | benzthiazol-2-yl | —CO—O— | |
| 1597 | benzisothiazol-3-yl | —CO—O— | |
| 1598 | isothiazol-3-yl | —CO—O— | |
| 1599 | isothioazol-4-yl | —CO—O— | |
| 1600 | isothiazol-5-yl | —CO—O— | |
| 1601 | 1,2,3-isodiazol-4-yl | —CO—O— | |
| 1602 | 1,2,4-thiadiazol-5-yl | —CO—O— | |
| 1603 | 1,3,4-thiadiazol-3-yl | —CO—O— | |
| 1604 | 2-furyl | —O—CO— | |
| 1605 | 5-nitro-2-furyl | —O—CO— | |
| 1606 | 5-chloro-2-furyl | —O—CO— | |
| 1607 | 3-furyl | —O—CO— | |
| 1608 | 5-nitro-3-furyl | —O—CO— | |
| 1609 | 5-chloro-3-furyl | —O—CO— | |
| 1610 | benzofuran-2-yl | —O—CO— | |
| 1611 | benzofuran-3-yl | —O—CO— | |
| 1612 | 2-thienyl | —O—CO— | |
| 1613 | 5-nitro-2-thienyl | —O—CO— | |
| 1614 | 5-chloro-2-thienyl | —O—CO— | |
| 1615 | 3-thienyl | —O—CO— | |
| 1616 | 5-nitro-3-thienyl | —O—CO— | |
| 1617 | 5-chloro-3-thienyl | —O—CO— | |
| 1618 | benzothien-2-yl | —O—CO— | |
| 1619 | benzothien-3-yl | —O—CO— | |
| 1620 | N-methyl-pyrrol-2-yl | —O—CO— | |
| 1621 | N-methyl-pyrrol-3-yl | —O—CO— | |
| 1622 | N-methyl-pyrazol-3-yl | —O—CO— | |
| 1623 | N-methyl-pyrazol-4-yl | —O—CO— | |
| 1625 | N-methyl-imidazol-2-yl | —O—CO— | |
| 1626 | N-methyl-imidazol-4-yl | —O—CO— | |
| 1627 | N-methyl-imidazol-5-yl | —O—CO— | |
| 1628 | 1-methyl-1,2,3-triazol-4-yl | —O—CO— | |
| 1629 | 1-methyl-1,2,3-triazol-5-yl | —O—CO— | |
| 1630 | 1-methyl-1,2,4-triazol-3-yl | —O—CO— | |
| 1631 | 1-methyl-1,2,4-triazol-5-yl | —O—CO— | |
| 1632 | 1-methyl-tetrazol-5-yl | —O—CO— | |
| 1633 | isoxazol-3-yl | —O—CO— | |
| 1634 | isoxazol-4-yl | —O—CO— | |
| 1635 | isoxazol-5-yl | —O—CO— | |
| 1636 | benzoisoxazol-3-yl | —O—CO— | |
| 1637 | benzoxazol-2-yl | —O—CO— | |
| 1638 | oxazol-2-yl | —O—CO— | |
| 1639 | oxazol-4-yl | —O—CO— | |
| 1640 | oxazol-5-yl | —O—CO— | |
| 1641 | thiazol-2-yl | —O—CO— | |
| 1642 | thiazol-4-yl | —O—CO— | |
| 1643 | thiazol-5-yl | —O—CO— | |
| 1644 | benzthiazol-2-yl | —O—CO— | |
| 1645 | benzisothiazol-3-yl | —O—CO— | |
| 1646 | isothiazol-3-yl | —O—CO— | |
| 1647 | isothiazol-4-yl | —O—CO— | |
| 1648 | isothiazol-5-yl | —O—CO— | |
| 1649 | 1,2,3-thiadiazol-4-yl | —O—CO— | |
| 1650 | 1,2,4-thiadiazol-5-yl | —O—CO— | |
| 1651 | 1,3,4-thiadiazol-3-yl | —O—CO— | |
| 1652 | 6-chloro-benzothiazol-2-yl | —SCH$_2$— | oil; $^1$H-NHR (CDCl$_3$): $\delta$ = 3.78(3H), 4.53(2H), 5.84(1H), 6.62(1H), 7.1–7.8(7H) |

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

Erysiphe graminis in cereals,
*Erysiphe cichoracearum* and *Sphaerotheca fuliginea* in cucurbits,
*Podosphaera leucotricha* in apples,
*Uncinula necator* in vines,
Puccinia species in cereals,
Rhizoctonia species in cotton and lawns,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, for example against Paecilomyces variotii.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 460 is mixed with 10 parts by weight of N-methyl-α-pyrrolidone. A mixture is obtained which is suitable for application in the form of very fine drops.

II. 20 parts by weight of compound no. 632 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 649 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 773 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 866 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 866 is intimately mixed with 97 parts by weight of particulate kaolin. A dust is obtained containing 3% by weight of the active ingredient.

VII 30 parts by weight of compound no. 460 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 632 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 649 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

The following list of fungicides with which the novel compounds may be combined is intended to illustrate possible combinations but not to impose any restrictions.

Examples of fungicides which may be combined with the novel compounds are:

sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;

nitro derivatives, such as dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;

heterocyclic substances, such as 2-heptadecylimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide, N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methylfuran-3-carboxanilide,
3 2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboximide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene, and various fungicides, such as dodecylguanidine acetate,
3-[3-(3,5-dimethyl-2-oxycyclohexyl)-2-hydroxyethyl]-glutaramide, hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLES

As comparative active ingredient, methyl α-phenylacrylate (A) disclosed in C.A. Reg. No. 1865-29-8 was used.

USE EXAMPLE 1

Action on *Pyricularia oryzae* (Protective)

Leaves of pot-grown rice seedlings of the "Bahia" variety were sprayed to runoff with aqueous emulsions consisting (dry basis) of 80% of active ingredient and 20% of emulsifier, and inoculated 24 hours later with an aqueous spore suspension of *Pyricularia oryzae*. The plants were then set up in climatic cabinets at 22° to 24° C. and a relative humidity of 95 to 99%. The extent of fungus spread was determined after 6 days.

The results show that active ingredients 460, 632, 649, 773 and 866, applied as 0.05 wt % spray liquors, had a better fungicidal action (95%) than prior art active ingredient A (60%).

USE EXAMPLE 2

Action on *Pyrenophora teres*

Barley seedlings of the "Igri" variety were sprayed to runoff at the two-leaf stage with aqueous suspensions consisting (dry basis) of 80% of active ingredient and 20% of emulsifier. After 24 hours the plants were inoculated with a spore suspension of the fungus *Pyrenophora teres*, and set up for 48 hours in a high-humidity climatic cabinet at 18° C. The plants were then cultivated for a further 5 days in the greenhouse at 20° to 22° C. and a relative humidity of 70° C. The extent of fungus spread was then assessed.

The results show that active ingredients 649 and 1439, applied as 0.05% spray liquors, had a better fungicidal action (90%) than prior art comparative compound A (0%).

USE EXAMPLE 3

Action on Wheat Mildew

Leaves of pot-grown wheat seedlings of the "Kanzler" variety were sprayed to runoff with aqueous liquors consisting (dry basis) of 80% of active ingredient and 20% of emulsifier, and dusted, 24 hours after the sprayed-on layer had dried, with spores or wheat mildew (*Erisyphe graminis* var. tritici). The plants were set up in the greenhouse at from 20° to 22° C. and a relative humidity of from 75 to 80%. The extent of mildew spread was determined after 7 days.

The results show that active ingredients 632 and 649, applied as 0.025% spray liquors, had a better fungicidal action (90%) than prior art comparative agent A (40%).

We claim:

1. α-Arylacrylates of the formula I

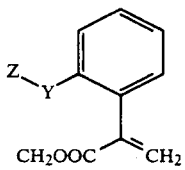

(I)

where

Y is substituted or unsubstituted $C_1$-$C_4$-alkylene, substituted or unsubstituted $C_2$-$C_4$-alkenylene, $C_2$-$C_4$-alkynylene, or $C_1$-$C_{10}$-alkyleneoxy, and Z is hydrogen, halogen, $C_1$-$C_{18}$-alkyl, $C_2$-$C_{18}$-alkenyl, $C_3$-$C_{18}$-cycloalkyl, $C_2$-$C_4$-alkynyl, aryl, aryl-$C_1$-$C_{10}$-alkyl, aryl-$C_2$-$C_{10}$-alkenyl, aryloxy, aryloxy-$C_1$-$C_{10}$-alkyl, $C_1$-$C_4$-alkoxy-$C_1$-$C_{10}$-alkyl, halo-$C_1$-$C_{10}$-alkyl, or aryloxy-$C_1$-$C_4$-alkoxy, which are unsubstituted or substituted by halogen, $C_1$-$C_4$-alkyl, $C_2$-$C_4$-alkenyl, $C_1$-$C_4$-alkoxy, $C_1$-$C_4$-haloalkyl, $C_2$-$C_4$-haloalkenyl, unsubstituted or substituted phenyl or unsubstituted or substituted phenoxy, with the proviso that Z-Y- is not $CH_3O$—.

2. A process for combating fungi, wherein the fungi, or the materials, plants, seed or the soil threatened by fungus attack are treated with a fungicidally effective amount of a compound of the formula I

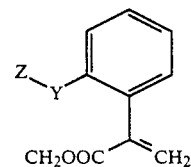

(I)

where

Y is substituted or unsubstituted $C_1$-$Ch_4$-alkylene, substituted or unsubstituted $C_2$-$C_4$-alkenylene, $C_2$-$C_4$-alkynylene, or $C_1$-$C_{10}$-alkyleneoxy, and Z is hydrogen, halogen, $C_1$-$C_{18}$-alkyl, $C_2$-$C_{18}$-alkenyl, $C_3$-$C_8$-cycloalkyl, $C_2$-$C_4$-alkynyl, aryl, aryl-$C_1$-$C_{10}$-alkyl, aryl-$C_2$-$C_{10}$-alkenyl, aryloxy, aryloxy-$C_1$-$C_{10}$-alkyl, $C_1$-$C_4$-alkoxy-$C_1$-$C_{10}$-alkyl, halo-$C_1$-$C_{10}$-alkyl, or aryloxy-$C_1$-$C_4$-alkoxy, which are unsubstituted or substituted by halogen, $C_1$-$C_4$-alkyl, $C_2$-$C_4$-alkenyl, $C_1$-$C_4$-alkoxy, $C_1$-$C_4$-haloalkyl, $C_2$-$C_4$-haloalkenyl, unsubstituted or substituted phenyl or unsubstituted or substituted phenoxy, with the proviso that Z-Y- is not $CH_3O$—.

3. A fungicide containing an inert carrier and a fungicidally effective amount of a compound of the formula I

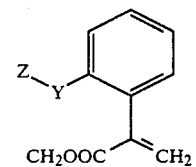

(I)

where

Y is substituted or unsubstituted $C_1$-$C_4$-alkylene, substituted or unsubstituted $C_2$-$C_4$-alkenylene, $C_2$-$C_4$-alkynylene, or $C_1$-$C_{10}$-alkyleneoxy, and Z is hydrogen, halogen, $C_1$-$C_{18}$-alkyl, $C_2$-$C_{18}$-alkenyl, $C_3$-$C_8$-cycloalkyl, $C_2$-$C_4$-alkynyl, aryl, aryl-$C_1$-$C_{10}$-alkyl, aryl-$C_2$-$C_{10}$-alkenyl, aryloxy, aryloxy-$C_1$-$C_{10}$-alkyl, $C_1$-$C_4$-alkoxy-$C_1$-$C_{10}$-alkyl, halo-$C_1$-$C_{10}$-alkyl, or aryloxy-$C_1$-$C_4$-alkoxy, which are unsubstituted or substituted by halogen, $C_1$-$C_4$-alkyl, $C_2$-$C_4$-alkenyl, $C_1$-$C_4$-alkoxy, $C_1$-$C_4$-haloalkyl, $C_2$-$C_4$-haloalkenyl, unsubstituted or substituted phenyl or unsubstituted or substituted phenoxy, with the proviso that Z-Y- is not $CH_3O$—.

* * * * *

UNITED STATES PATENT AND TRADEMARK OFFICE
CERTIFICATE OF CORRECTION

PATENT NO. : 5,041,618

DATED : August 20, 1991

INVENTOR(S) : Siegbert Brand et al.

It is certified that error appears in the above-identified patent and that said Letters Patent is hereby corrected as shown below:

On the title page:
    The Priority data has been omitted, should be,

--June 25, 1988 [DE] Fed. Rep. of Germany ........3821503--.

Signed and Sealed this

Thirteenth Day of April, 1993

*Attest:*

STEPHEN G. KUNIN

*Attesting Officer*      *Acting Commissioner of Patents and Trademarks*